US006329340B1

(12) United States Patent
Bougueleret et al.

(10) Patent No.: US 6,329,340 B1
(45) Date of Patent: Dec. 11, 2001

(54) HUMAN DEFENSIN DEF-X

(75) Inventors: Lydie Bougueleret, Vanves; Ilya Chumakov, Vaux-le-Penil, both of (FR)

(73) Assignee: Genset S.A. (FR)

( * ) Notice: Subject to any disclaimer, the term of this patent is extended or adjusted under 35 U.S.C. 154(b) by 0 days.

(21) Appl. No.: 09/486,580

(22) PCT Filed: Aug. 28, 1998

(86) PCT No.: PCT/EP98/01864

§ 371 Date: Feb. 25, 2000

§ 102(e) Date: Feb. 25, 2000

(87) PCT Pub. No.: WO99/11663

PCT Pub. Date: Mar. 11, 1999

(30) Foreign Application Priority Data

Aug. 29, 1997 (FR) .................................................. 97 10823

(51) Int. Cl.[7] .......................... A61K 38/16; A61K 38/17; C07K 14/00; C07K 14/435
(52) U.S. Cl. .................................... 514/12; 514/1; 514/2; 514/885; 514/886; 514/887; 530/300; 530/324
(58) Field of Search .................................. 530/300, 324; 514/1, 2, 12, 885, 886, 887

(56) References Cited

U.S. PATENT DOCUMENTS

| 5,242,902 | 9/1993 | Murphy et al. . |
| 5,641,497 | 6/1997 | Bevins et al. . |

FOREIGN PATENT DOCUMENTS

| WO 89/11291 | 11/1989 | (WO) . |
| WO 94/21672 | 9/1994 | (WO) . |
| WO 95/32287 | 11/1995 | (WO) . |

OTHER PUBLICATIONS

GenBank Accession No. U18745 (Human corticostatin/defensin HP–4 gene) 1995.*

Bevins et al. (1996) Human Enteric Defensin Genes: Chromosomal Map Position and a Model for Possible Evolutionary Relationship, Genomics, 31:95–106.

Ganz et al. (1994) Defensins, Current Opinion in Immunology 6:584–589.

Ganz et al. (1995) Defensins, Pharmac Ther. 66:191–205.

Kagan et al. (1994) Defensins: a Family of Antimicrobial and Cytotoxic Peptides, Toxicology 87:131–149.

Lehrer et al. (1992) Defensins: Endogenous Antibiotic Peptides from Human Leukocytes, Ciba Foundation Symposium 171:276–293.

Mallow et al. (1996) Human Enteric Defensins, The Journal of Biological Chemistry 271:4038–4045.

Martin et al. (1995) Defensins and Other Endogenous Peptide Antibiotics of Vertebrates, Journal of Leukocyte Biology 58:128–136.

Sparkes et al. (1989) Assignment of Defensin Gene(s) to Human Chromosome 8p23, Genomics 5:240–244.

White et al. (1995) Structure, Function, and Membrane Integration of Defensins, Current Opinion in Structural Biology 5:521–527.

Wilde et al. (1989) Purification and Characterization of Human Neutrophil Peptide 4, a Novel Member of the Defensin Family, Journal of Biological Chemistry 264:11200–11203.

Hughes, A.L. [1999] "Evolutionary Diverisfication of the Mammalian Defensins," *CMLS. Cell. Mol. Life Sci.* 56:94–103.

Hughes, A. et al. [1997] "Coordinated Amino Acid Changes in the Evolution of Mammalian Defensins," *J Mol Evol* 44:675–82.

Lerner, R. [1982] "Tapping the Immunological Repertoire to Produce Antibodies of Predetermined Specificity," *Nature* 299:592–96.

Raj, P. [2000] "Large–scale Synthesis and Functional Elements for the Antimicrobial Activity of Defensins," *Biochem J* 347:633–41.

* cited by examiner

*Primary Examiner*—Phillip Gambel
*Assistant Examiner*—Jessica H. Roark
(74) *Attorney, Agent, or Firm*—Saliwanchik, Lloyd & Saliwanchik

(57) ABSTRACT

The present invention relates to a human polypeptide defensin Def-X, homologous to HNP-4, its genomic DNA and cDNA, vectors, cells transformed with said vectors, the use of said polypeptides as antibiotic, cytotoxic, repair and endocrine regulatory agent and as pesticide as well as cosmetic or pharmaceutical compositions for the treatment of microbial infections, in particular bacterial, fungal and viral infections, or parasitic infections, cancers, of inflammation and of immune deficiency. Finally, the invention comprises diagnostic methods and kits for the determination of a microbial or parasitic infection and of an inflammation, or for screening for predisposition to immune deficiencies or cancer diseases.

56 Claims, 16 Drawing Sheets

| | | | | | |
|---|---|---|---|---|---|
| ACACCATTTG | TCTTCATGTA | ACCCCATTAG | CTATACCCTC | TAGTGCAAGG | AAACCATAGG |
| 10 | 20 | 30 | 40 | 50 | 60 |
| GCCTAGGTCA | CACCATGAGG | CTGCNCTTAC | AAGTTATGCA | AAAACTATGG | ACTTGGGAGA |
| 70 | 80 | 90 | 100 | 110 | 120 |
| CCTGTGCGTA | ACAACATCAC | ACNCCAAATT | TAACCAGCTC | TCCCCATAAC | AGCACGCTCA |
| 130 | 140 | 150 | 160 | 170 | 180 |
| TGTGTTACTG | AGGAAATGCC | TGTGGATTGG | AGTGTGTTCT | GTGTGCAGGA | GGCTGGTCCA |
| 190 | 200 | 210 | 220 | 230 | 240 |
| GGTTTCACTT | CTGCAGGACA | CTGGACGTTT | CCCAAAACCA | GCAGACTTTC | CCCACGTGCA |
| 250 | 260 | 270 | 280 | 290 | 300 |
| CACACACCCC | TTCTCATTTT | GCCTCTACAT | CCATATCCAC | TGGGCCCTTC | AGGCACCTAC |
| 310 | 320 | 330 | 340 | 350 | 360 |
| TAATGCCCTA | GAACCTAAAA | CCATCATCTG | GGGCCCAGTT | CCCTGAATGG | CCCTAATCTC |
| 370 | 380 | 390 | 400 | 410 | 420 |
| TTCCTCTGCT | GGAATGAGTC | CAGTGCCCAC | TTCCTCCAAC | GGTGAAATTG | CTGGGCTGCT |
| 430 | 440 | 450 | 460 | 470 | 480 |
| ACAGATCAGG | AACTCACTGC | TTCCTCATAG | GGGCAGCCGA | CTTCACTGCT | CTGCAACAGC |
| 490 | 500 | 510 | 520 | 530 | 540 |
| GACCACCCCT | AGCGAGGCTT | GAGATGCCTC | TTGCCTCCTT | AAGACTGAGG | GAGACGCTTC |
| 550 | 560 | 570 | 580 | 590 | 600 |
| AGCTCTCACT | CCACTGCCCC | AAGTCCTCCA | CAGCGCGGTG | CCTGCTGCCT | TCACACAGAG |
| 610 | 620 | 630 | 640 | 650 | 660 |
| CTGCAGGGGN | AGGTCCTGTG | TATCCGGCCT | GCTGGACCAG | CGCTGTGCAC | AACCCTCCCA |
| 670 | 680 | 690 | 700 | 710 | 720 |
| TGGCAACAGT | GGCTGCCCGG | CCTGCACACT | GGGCTTGGCA | ACCTCGCTGT | AGGTATTTAT |
| 730 | 740 | 750 | 760 | 770 | 780 |
| TCCCTCAGGA | GTGACTGCAT | TCTTTTCCCA | TTTCAGAAA | ACTGATGCCA | TTTACCTCAC |
| 790 | 800 | 810 | 820 | 830 | 840 |
| TATGAGGAGG | AGGAGGAGGA | GGAGGGTGGA | GAGTGGTACA | TTTTAAAATG | TGCACTATTC |
| 850 | 860 | 870 | 880 | 890 | 900 |
| TCCCTAGGAC | TCCCCCTCAA | ATAACCCAGG | AGGGACCATA | CCAGCTCATT | CCTGTGTATC |
| 910 | 920 | 930 | 940 | 950 | 960 |
| CCAAGCATAN | GAGTAATCAT | CCCACTCATG | CTGAGTGTAT | GGTGGCCATT | AAGCCTGCCC |
| 970 | 980 | 990 | 1000 | 1010 | 1020 |

FIG. 1A

```
TGAACTGGCT TTAGAACAAG GTGTTTGAGC ACACAGCACC GTCTTGCTGC CACCTTGGCC
    1030       1040       1050       1060       1070       1080

CCCTCCCTTG TGAGACCTCT GAGACACATT NAGGTCTCAC CTAAAAATCT CAGGATTTCT
    1090       1100       1110       1120       1130       1140
AGGCCCAAAN CGGTCCTAAA AAATTGTTCA GTCTGAACTC TCTAAGGTCA AGAGAAGAGG
    1150       1160       1170       1180       1190       1200

TGGTTGCTCC CTCTAAGAAA CCACATGTTG CATGTACATC CTTAATTCCG GAAAGTCCAA
    1210       1220       1230       1240       1250       1260

CAAACCTGCC CTGCTTAGCA ACACAAGCCG AGGTGGTACT CCTCTCACCC GGGCATTCTC
    1270       1280       1290       1300       1310       1320

CAACACACCT GTTTGTCCAA ACAGCTTTGA TTTGTTTTTA TAGTTGGACC CCAGGTTCCC
    1330       1340       1350       1360       1370       1380

AGGAGGCTGG TTCAGGCCAT ATTCCAAATC CTCATCTGTG TGTGAGTGGC ATTCTTAGCC
    1390       1400       1410       1420       1430       1440

TAGCCTCCTT ACAGGGTGGA TACTATGATA CACAGCCAGG CTGTCCCAGT GGCTTTCAAT
    1450       1460       1470       1480       1490       1500

ATTCTTTTGG TCCAGATAGT TCAGCCTCAG CACCAGTGTA GGCATCACAG GGTCAATTGT
    1510       1520       1530       1540       1550       1560

CTTAGGAGTC ATGGAGAATT CATAGTTGGT AGCTACCTGG GCCTGGCCAG GGCTGACCAT
    1570       1580       1590       1600       1610       1620

AGACAAGGCA TCCCTCTGTG AACTCCTATT TTAATGCCAG CTTCCCAACA AATTTCTCAA
    1630       1640       1650       1660       1670       1680
                                          CAAT box
                                          ----
CTGCTCTTAC CAGCAGGTAT TTAAACTACT CAATAGAAAG TAACCCTGAA AATTAGGACA
    1690       1700       1710       1720       1730       1740
              TATA box
              ----------
CCTGTTCCCA AAAGACCCTT AAATAGGGGA AGTCCTTTCN CTGCTTGTGC ACAGCTGCTG
    1750       1760       1770       1780       1790       1800

|->mRNA -------------------
ATGTGGCAAC ATGAGGCCTG GGACAGGGGA CTGTCCTCTG CCCACTCTGG TAGCCTCACG
    1810       1820       1830       1840       1850       1860
              Spsite
-- exon 1 ---->######
TAGCTTAACA ATCTGTCAGT AATACAATAC AAAACTTAAA CTTTCATACT GCGGTTCCAC
    1870       1880       1890       1900       1910       1920

CCAGGAAGCT GTGTTCCCAA TCTGACCCGT GATTATGGGG CCACCTCAGA GGGNACCCAG
    1930       1940       1950       1960       1970       1980
```

FIG. 1B

```
TGAGGGAATA TTTTGCCATC TGGGACTGTT GGTTGCTGGG GGCAGTGGCT ATGAGCTCAG
    1990       2000       2010       2020       2030       2040

TTAATAAACT CAAGCAGTTT CCTTCCAAAC ACACATGTCC TACTTAACGT GTCCAACAGA
    2050       2060       2070       2080       2090       2100

------
GATGATCATA CTCATANGCT GCTAAAACAT TANTTTTATT TTGAGAAAAG TCTATTCATG
    2110       2120       2130       2140       2150       2160
--------------------- Alu insert ---------------------------------
TTCTTGGCCC ATGGAGTTTT CATTTNATTA NTTTATTTAT TTTGCAGAGA TGGAGTCTCA
    2170       2180       2190       2200       2210       2220

- - - - - - - - - - - - - - - - - - - - - - - - - - - - - - - -
CTATGTTGCT CAAGCTGGTC TCCAACTCCT GGGCTCAAGC GATCTTCCTA CTTTGGCCTT
    2230       2240       2250       2260       2270       2280

- - - - - - - - - - - - - - - - - - - - - - - - - - - - - -
TGAAAGCGCT GAGATTGCCT GTGTGAGCCA TCATGGGGGC TCACTGGCCC ACTGATTAAT
    2290       2300       2310       2320       2330       2340

CAGATTAATT GTTTTTTGCT ATTGAANTTG TTTGACTTCC TTGTATATTC GGATATTTAC
    2350       2360       2370       2380       2390       2400

CCATTCTAAC ACGTAGGGTT TGCAAATATT TTCTCTCATG TTCTGTGTTG CCTTTTCACT
    2410       2420       2430       2440       2450       2460

CAGTTGATGG TTTCCTTTGC TGTGCAGGTG CTTTAGTGTT CAACGCAGCC CCGCTTGTCT
    2470       2480       2490       2500       2510       2520

ATTTTCCATT TTATTGCCTG TCCCTTTGAT GTCATAGCCA AGAAATAATT GCCCAGATTA
    2530       2540       2550       2560       2570       2580

ATGTCAAAAA GCTTTATCCC TATATATTCT TCTAGTAGTT TATGGTTTCA GATCTTATGT
    2590       2600       2610       2620       2630       2640

TTAGGTCTTC AATCCATTGA GTTGATTTTT GTATGTGGTA TAAGAAAAAA GACCACATGT
    2650       2660       2670       2680       2690       2700

ATACATATCT CAAATTCTAA GGTAGTATAT ATTAGACACA TACAATGTGT CTATTTACAC
    2710       2720       2730       2740       2750       2760

ACATTGAGCT GAAAATAATA AACATATTTT TATCTTTCAA TCAACTCTAT CTCTATCTCA
    2770       2780       2790       2800       2810       2820

CTGAACTTGT TTCACCTATA GCCTGATGAG GTTGCTGTCC TCTCTACCCC AGCTCCTATA
    2830       2840       2850       2860       2870       2880

GGAGACTGCT CATCCCCTAA CCTCAAAAAC CCCTTCATGA GGGTGATAAT GCCCTTGAAT
    2890       2900       2910       2920       2930       2940
```

FIG. 1C

```
CCTGCAATGA ATTAGTTCTC TACTACAGTG GAATTCAGGT CTGTTATGAG GGTCTGGATC
     2950       2960       2970       2980       2990       3000

TCTGAAGAGA AGAGCTCTCA TTTTCAGAAA ATAAGCAGGA TTTATTCCCT GAAATTACTG
     3010       3020       3030       3040       3050       3060

AATTAAATCA CTGTTTCGAT TACTTTTTGC AATATTAAAA GTAAATATTT AAACAGGTAA
     3070       3080       3090       3100       3110       3120

AAACAGAAAT AATGGTAGGG TCCTTATCAT CACCGTGAAT TCCAAGCTAG CATAGACACT
     3130       3140       3150       3160       3170       3180

AAACCTAGAG ATTCACACTA GAATGAAAGC TGGGAGAGCA GAGGAGTCTC AGAAGGATGT
     3190       3200       3210       3220       3230       3240

GGAGGCCAAT GGACACCTGC AACCTCTCCA ACGAAATGCC TACCTCCTCT CACTGCAGCA
     3250       3260       3270       3280       3290       3300

TCCATCTCTG AGCCTTCTCG CAGCAGAGCT ATAAATTCAG CCTGGCTCCT CCGTTCCCAC
     3310       3320       3330       3340       3350       3360

Spsite              CDS start
                                  ###<---------------***--------------
ACATCCACTC CTGCTCTCCC TCCTCTCCTC CAGGTGACTA CAGTTATGAG GACCCTCACC
     3370       3380       3390       3400       3410       3420

---------------------- Exon 2 ------------------------------
CTCCTCTCTG CCTTTCTCCT GGTGGCCCTT CAGGCCTGGG CAGAGCCGCT CCAGGCAAGA
     3430       3440       3450       3460       3470       3480

------------------------------------------------------------
GCTCATGAGA TGCCAGCCCA GAAGCAGCCT CCAGCAGATG ACCAGGATGT GGTCATTTAC
     3490       3500       3510       3520       3530       3540

Spsite
-------------------------------------------->### ###
TTTTCAGGAG ATGACAGCTG CTCTCTTCAG GTTCCAGGTG AGAGATGCCA GCATGCAGAG
     3550       3560       3570       3580       3590       3600

CTACAGACTA GACAGAAGGA CAGGAGACAG GCTCTGGAAT TGGATCTCAG TGGCAGATGT
     3610       3620       3630       3640       3650       3660

CACTTAGGTG GCTATACTTA ACATCTCTGG TCCTGGATTT TCTCATATCT AAATGGAATA
     3670       3680       3690       3700       3710       3720

GAGAACCAAA GAAATCTAAG AGATTTTTCT TTCTCCAAAA ACTTGATTCC AAGATATGAC
     3730       3740       3750       3760       3770       3780

TGTGAAATTC ACTAGATTTA AGATATAAGG AGATGCTACC TAGTTCCTTC TGGAGCCAGA
     3790       3800       3810       3820       3830       3840
```

FIG. 1D

```
CAAACAAGCT TAAGTATATA GGAAAATATT TCACCCTGTC TATATAGGAG GTTTTAGAAC
    3850       3860       3870       3880       3890       3900

CTGGAGAGGA GCCTAAGAAT GTGTTCAGGT GTGTGTGTGA TGGGCAGGAA TGCAGAAAAG
    3910       3920       3930       3940       3950       3960

TGAAGCAAAG GAGAATGAGT CTCGAATCCT GTGTGACCAG CACTGCTCTG TGTATTTATT
    3970       3980       3990       4000       4010       4020

CCTATTGACT GAGATTGTTT GTGCTACCGG CTGTAATACA GCCAACATCA CTCATCAGCC
    4030       4040       4050       4060       4070       4080

AACATGTGAC TTCTCCAAGA TTCCCTTTAC CACCCACTGC TGNACCCCGT ACTCAGTTTC
    4090       4100       4110       4120       4130       4140
                                Spsite
                                ###<---------------------------------
TGATGCTCTC TCTGGGTCCC CAGGCTCAAC AAAGGGCTTG ATCTGCCATT GCAGAGTACT
    4150       4160       4170       4180       4190       4200

------------------------ Exon 3 ------------------------
ATACTGCATT TTTGGAGAAC ATCTTGGTGG GACCTGCTTC ATCCTTGGTG AACGCTACCC
    4210       4220       4230       4240       4250       4260
                CDS stop
----------------***--------------------------------------------
AATCTGCTGC TACTAAGCTT GCAGACTAGA GAAAAAGAGT TCATAATTTT CTTTGAGCAT
    4270       4280       4290       4300       4310       4320

Poly Ad
                                                        ******
-------------------------------------------------------------->
TAAAGGGAAT TGTTATTCTT ATACCTTGTC CTCGATTTCC TGTCCTCATC CCAAATAAAT
    4330       4340       4350       4360       4370       4380

ACTTGGTAAC ATGATTTCCG GGTTTTTTTT TTTTT
    4390       4400       4410
```

FIG. 1E

```
        10        20        30        40        50
DEF4 GGATCCCCATTTGTCTTCAGTGTAACCC-ATTAGTTAAACCGCCTACTGCAAGGAAACCA
       : :::::::::::::: :::::::: ::::: :: :::   :::  :::::::::::::
DEFX     ACACCATTTGTCTTCA-TGTAACCCCATTAGCTATACCCTCTAGTGCAAGGAAACCA
           10        20        30        40        50

60        70        80        90       100       110
DEF4 CAAGGCTTGGATCAGATCATGAGGCTGCCCT-ACAAGTTATGCCAAAAAATATGGACTTG
     :  ::: : : :::  : ::::::::::::.:: :::::::::::: ::::: ::::::::
DEFX TAGGGCCTAGGTCACACCATGAGGCTGCNCTTACAAGTTATGC-AAAAACTATGGACTTG
        60        70        80        90       100       110

120       130       140       150       160       170
DEF4 GAAGACCTGTCTGTTATAATATCACAC-CCAAATCTAACCAGCTCTGCCAATAACAGCTC
     : ::::::::: :: :: :::::::::  ::::: :::::::::::::: :::::::::  :
DEFX GGAGACCTGTGCGTAACAACATCACACNCCAAATTTAACCAGCTCTCCCCATAACAGCAC
       120       130       140       150       160       170

180       190       200       210       220       230
DEF4 TCTCCTATGTTACTAGGAAAATGCCTATGGATTGGAGTGTGTTCTGTGTGCAGGAGGCTG
     ::: : ::::::::  : ::::::::: ::::::::::::::::::::::::::::::::
DEFX GCTCATGTGTTACTGAGGAAAATGCCTGTGGATTGGAGTGTGTTCTGTGTGCAGGAGGCTG
       180       190       200       210       220       230

240       250       260       270       280       290
DEF4 GTCCAGGTTTCACTTCTGCAGGACACTGGACATC-CCACAACCACCAGACCTTCCCCAC
     ::::::::::::::::::::::::::::::::::: :   :::: ::::: ::::: ::::::::
DEFX GTCCAGGTTTCACTTCTGCAGGACACTGGACGTTTCCCAAAACCAGCAGACTTTCCCCAC
       240       250       260       270       280       290

300       310       320       330       340       350
DEF4 GTGCACACACACCCCTTCTCATTTTGCCTCTACATCCATATCCACTGGGCCCTTCAGGCA
     ::::::::::::::::::::::::::::::::::::::::::::::::::::::::::::
DEFX GTGCACACACACCCCTTCTCATTTTGCCTCTACATCCATATCCACTGGGCCCTTCAGGCA
       300       310       320       330       340       350

360       370       380       390       400       410
DEF4 CCTACTAATGCCCTAGAACCTAAAACCATCATCTGGGGCCCAGTTCCCCAAATAGCCCTA
     :::::::::::::::::::::::::::::::::::::::::::::::::: :::  ::::::
DEFX CCTACTAATGCCCTAGAACCTAAAACCATCATCTGGGGCCCAGTTCCCTGAATGGCCCTA
       360       370       380       390       400       410

420       430       440       450       460       470
DEF4 ATTTCTTCCTCTGCTGGAATGAGTCCAGTGCCCACTTCCTCCAAAGGTGAAATTGCTGGG
     ::  :::::::::::::::::::::::::::::::::::::::::: ::::::::::::::
DEFX ATCTCTTCCTCTGCTGGAATGAGTCCAGTGCCCACTTCCTCCAACGGTGAAATTGCTGGG
       420       430       440       450       460       470

480       490       500       510       520       530
DEF4 CCTGCAACAGATCAGGAACTCACTGCTTC-TCATAGGGGCAGCCGACTTCACTGCTCTGG
     :  :::  :::::::::::::::::::::::: ::::::::::::::::::::::::::::::
DEFX C-TGCTACAGATCAGGAACTCACTGCTTCCTCATAGGGGCAGCCGACTTCACTGCTCTGC
        480       490       500       510       520       530
```

FIG. 2A

```
          540       550       560       570       580       590
DEF4 AACAGCGACCACCCCTAGCGAGGCTTGAGATGCCTCTTCCCTCCTTAAGACTGAGAGCGC
     ::::::::::::::::::::::::::::::::::::::::::: :::::::::::::: : :
DEFX AACAGCGACCACCCCTAGCGAGGCTTGAGATGCCTCTTGCCTCCTTAAGACTGAGGGAGA
          540       550       560       570       580       590

600       610       620       630
DEF4 CGCT---------------GCCCCCAGTCCTCCATAGCCCAGTGCCTGGCTGCCTTCA
     ::::           ::::: :::::::::: ::: : ::::::: :::::::::
DEFX CGCTTCAGCTCTCACTCCACTGCCCCAAGTCCTCCACAGCGCGGTGCCTG-CTGCCTTCA
          600       610       620       630       640       650

640       650       660       670       680       690
DEF4 GCCAGAGCTGCAGGGG-AGGCCCTGAGCACCCAAGTCCTGCTGGACCAGCGCTGTGCACG
     :::::::::::::::: ::: :::: : : :: : :::::::::::::::::::::::::
DEFX CACAGAGCTGCAGGGGNAGGTCCTGTGTATCC--GGCCTGCTGGACCAGCGCTGTGCACA
          660       670       680       690       700       710

700       710       720       730       740       750
DEF4 GCCCTCCCATGGCGGCAGGGGCTGCCTGGACTGCATACTGGGTTCAGCAACCTCACTATA
     :::::::::::: ::: :::::::: ::::: :::::: : ::::::::: :: :: ::
DEFX ACCCTCCCATGGCAACAGTGGCTGCCCGGCCTGCACACTGGGCTTGGCAACCTCGCTGTA
          720       730       740       750       760       770

760       770       780       790       800       810
DEF4 GGTATTCATTCCCTCAGGAACAACTGCATTCTTTTCTCATTTCCAGAAACCTCATCCCGT
     :::::: :::::::::::  ::::::::::::::::  :::::::::::: :: :: :: :
DEFX GGTATTTATTCCCTCAGGAGTGACTGCATTCTTTTCCCATTTCCAGAAAACTGATGCCAT
          780       790       800       810       820       830

820       830       840                 850       860
DEF4 TTACCTCACTACAAGGAGGAGGATG--------GTGGAGAGTGGTACATTTTAAAATGT
     ::::::::::: ::::::::: :          :::::::::::::::::::::::::::
DEFX TTACCTCACTATGAGGAGGAGGAGGAGGAGGGTGGAGAGTGGTACATTTTAAAATGT
          840       850       860       870       880       890

870       880       890       900       910       920
DEF4 GCACTAGTCTCCCTGGGACTCCCCTTCAAATAACCCAGGAGGGACCACACAAGGGAAAGC
     ::::: :::::::: :::::::::: ::::::::::::::::::::: :: ::   :  :
DEFX GCACTATTCTCCCTAGGACTCCCCCTCAAATAACCCAGGAGGGACCATACCAGCTCATTC
          900       910       920       930       940       950

930       940       950       960       970       980
DEF4 TTATGCATCCCCCCCACCC-AGTGACCATCTTCCTAACTCTGGGTGTAGGGAGACTCGTA
     : :: :::::    ::  . :::  :::: ::  : :::  ::::: :: : :    ::
DEFX CTGTGTATCCCAAGCATANGAGTAATCATCCCACTCATGCTGAGTGTATGGTGGCCATTA
          960       970       980       990       1000      1010

990       1000      1010      1020      1030      1040
DEF4 AGCCTACG--GGATTGGTTTGGGAACAGGGTATTTGAGCTCACAACACAAGGTGATGCAA
     :::::: :   : :::  :: ::: :::::: :::::::  :::: ::::: :::: :::
DEFX AGCCTGCCCTGAACTGGCTTTAGAACAAGGTGTTTGAGCACACAGCACCG---------
          1020      1030      1040      1050      1060
```

FIG. 2B

```
             1050        1060       1070       1080       1090       1100
DEF4  GCTAACACCAATCTCGCTGCAGCTTTGGCCACCATCCTAAGG-GACTTCTGACAGACATT
      :::  :::::  :  :  ::::: ::   :::     : :::  :::::  :  :::::
DEFX  ----------TCTTGCTGCCACCTTGGCCCCCTCCCTTGTGAGACCTCTGAGACACATT
                     1070       1080       1090       1100       1110

1110       1120       1130       1140       1150       1160
DEF4  -AGGTGTCACGCAATCATTTGATGAGTCCTTGGCCTGGAT--GACCTAGACAGTCATTTA
       ::::  ::::  ::   ::  :  ::   :: :: ::::    :   :::::  :  :
DEFX  NAGGTCTCACCTAAAAATCTCAGGATTTCTAGGCCCAAANCGGTCCTAAAAAATTGTTCA
            1120       1130       1140       1150       1160       1170

1170       1180       1190       1200       1210       1220
DEF4  GGCTTGAACTATCTAAGGCCAAGCAAAAAGGTGACTGTCCCCTCTAGGAA-CCACATGCT
      :  ::  :::::  :::::::   ::::   ::  ::::::  :::::::: :::::::  :
DEFX  GTCT-GAACTCTCTAAGGTCAAGAGAAGAGGTGGTTGCTCCCTCTAAGAAACCACATGTT
            1180       1190       1200       1210       1220

1230       1240       1250       1260       1270
DEF4  ATATGCACATCCTTTACTCGGGAGCCTGCAAC----CTGCCCTATCCAGCAACACAAGCC
       :::  :::::::: :  ::: :::    :  ::::         ::::::::::::::
DEFX  GCATGTACATCCTTAATTCCGGAAAGTCCAACAAACCTGCCCTGCTTAGCAACACAAGCC
         1230       1240       1250       1260       1270       1280

1280       1290       1300       1310       1320       1330
DEF4  CAGGCG-TATTCAGTCTCATCCAGGTATTCTCCAAC---CTTACTTGTCTGAATGGCTTG
      :::  :  :::: ::  :::::  :::::::::: :   : :  :::::  ::   ::::
DEFX  GAGGTGGTACTCC-TCTCACCCGGGCATTCTCCAACACACCTGTTTGTCCAAACAGCTTT
        1290       1300       1310       1320       1330       1340

1340       1350       1360       1370       1380       1390
DEF4  GATTTGTTTTTATGGTTAGACCCCAGGG-CCTGGGAGGTCAGTTCAGACCACATTCCAAA
      ::::::::::::::: ::: ::::::::  :::  ::::::::::::::  :::::::::
DEFX  GATTTGTTTTTATAGTTGGACCCCAGGTTCCCAGGAGGCTGGTTCAGGCCATATTCCAAA
         1350       1360       1370       1380       1390       1400

1400       1410       1420       1430       1440       1450
DEF4  TCCTCATCTGTGTGTGGGTGGCATTTTGATCCTAGTCTCCTCGCAAGGTGTATACAACAA
      :::::::::::::::::: ::::::: : : ::::: :::::  :: ::::  ::::  ::
DEFX  TCCTCATCTGTGTGTGAGTGGCATTCTTAGCCTAGCCTCCTTACAGGGTGGATACTATGA
         1410       1420       1430       1440       1450       1460

1460       1470       1480       1490       1500       1510
DEF4  TATGCAGGCCAGGCTCTCCTGGTGGCTTTAAATATTCCCTCGGTCCAGGTAGTTCAGCCT
      ::  ::: ::::::::: :::  ::::::::  ::::::: : ::::::: :::::::::::
DEFX  TACACAG-CCAGGCTGTCCCAGTGGCTTTCAATATTCTTTTGGTCCAGATAGTTCAGCCT
        1470       1480       1490       1500       1510       1520

1520       1530       1540       1550       1560       1570
DEF4  CAGCCACCAGCATAGGTATCATGGGTCAATTGTCTTAGGAGTCATGAGGAATCCACAGT
      ::::  ::::  ::::  ::::  ::::::::::::::::::::::::  :::: ::  :::
DEFX  CAGC-ACCAGTGTAGGCATCACAGGGTCAATTGTCTTAGGAGTCATGGAGAATTCATAGT
         1530       1540       1550       1560       1570       1580
```

FIG. 2C

```
              1580       1590       1600       1610       1620       1630
DEF4   TGATTGCTGCCTGGGCCTGGCCAGGGCTGACCAAAGTAGACGAGGGGTCGGTACCTCCGT
       :: :  :::   :::::::::::::::::::::::       :::::  :::   ::     ::::  ::
DEFX   TGGTAGCTACCTGGGCCTGGCCAGGGCTGACCA---TAGACAAGGCATC----CCTCTGT
          1590      1600       1610       1620       1630

1640       1650       1660       1670       1680       1690
DEF4   GGACTCCTGCTTGAACTCCAGCTTTCTGCCAAATTTCTCAACTGCCCTTGTTAACAGTTA
       :  ::::::  ::  ::  ::::::::  :    ::::::::::::::::  :  :::  ::
DEFX   GAACTCCTATTTTAATGCCAGCTTCCCAACAAATTTCTCAACTGCTCTTACCAGCAGGTA
       1640       1650       1660       1670       1680       1690

CAAT box                              -
              1700   ----1710       1720       1730       1740       1750
DEF4   TTTAAAGTACCCAATAGAAAGTAACGCTGAAAAATTAGGACACCTGATACCAAAAGACCC
       ::::::: :::  :::::::::::::::: ::::::: :::::::::::: : :::::::::::
DEFX   TTTAAACTACTCAATAGAAAGTAACCCTGAAAA-TTAGGACACCTGTTCCCAAAAGACCC
       1700       1710       1720       1730       1740       1750

TATA box
           ----------      1770       1780       1790       1800
DEF4   TTAAATAAGG-AAGTCCTCTC-CTCTGTGTGCATGGCTGCTCTTG---CTACATAAGACC
       ::::::::  :: :::::::  ::  ::     ::::::   ::::::  ::     :  ::::  ::  ::
DEFX   TTAAATAGGGGAAGTCCTTTCNCTGCTTGTGCACAGCTGCTGATGTGGCAACATGAGGCC
       1760       1770       1780       1790       1800       1810 mRNA start -->                           SpSite
              1810       1820     |  1830       1840       1850       1860   ----
DEF4   TGGAACACAGGACTGCTGTCTGCCCTCTCTGCTCGCCCTGCCTAGCTTGAGGATCTGTAA
       ::: :::  ::::::   :::::::  :::::::: :  :::      :  :::::::   :   :::::::: :
DEFX   TGGGACAGGGGACTGTCCTCTGCCCACTCTGGTAGCCTCACGTAGCTTAACAATCTGTCA
       1820       1830       1840       1850       1860       1870

--         1880       1890       1900       1910       1920
DEF4   GTAACACAA-----AACTTAAACTTTCACATTGAGGTTTCAATATTGAAGCTGTGTCCCC
       ::::  ::::          :::::::::::::::::  :::  ::::  ::         ::::::::::  :::
DEFX   GTAATACAATACAAAACTTAAACTTTCATACTGCGGTTCCACCCAGGAAGCTGTGTTCCC
       1880       1890       1900       1910       1920       1930

1930       1940       1950       1960       1970       1980
DEF4   AGTCTGACCTCTCACTGTGGGGCCACCCCAGAGGACCCAGCGTGAAGCCCCTGCTGTGAA
       : :::::::  :  :  : ::::::::::  ::::::  .  :  ::::  :       :    :  ::
DEFX   AATCTGACCCGTGATTATGGGGCCACCTCAGAGGGNACCCAGTGAGGGAA-TATTTTG--
       1940       1950       1960       1970       1980       1990

1990       2000       2010       2020       2030       2040
DEF4   CTTCTATCTGGGTGTCTGGCGGCTGCTGGGGGTAATGGCTACTAGCTAAGTCAATAGAGA
       :  :::::::   :::   ::  ::::::::::::  :  ::::::   ::::  :::  ::::
DEFX   ---CCATCTGGGA--CTGTTGGTTGCTGGGGGCAGTGGCTATGAGCTCAGTTAATA----
              2000       2010       2020       2030       2040
```

FIG. 2D

```
              2050      2060      2070      2080      2090      2100
DEF4  AACTCAAAAAGTTTCCTTCCAAACACACGTGTCCTACTTGACATGTCCAATAAAGACGAT
      :::::::    ::::::::::::::::: ::::::::::: ::  :::::::  :  ::: :::
DEFX  AACTCAAGCAGTTTCCTTCCAAACACACATGTCCTACTTAACGTGTCCAACAGAGATGAT
      2050      2060      2070      2080      2090      2100

2110      2120      2130      2140
DEF4  CA----CAGCTTCT--TAAAACATTA-TTTTATTGTGAGAGAAGCCTCT-----------
      ::    ::  . ::  :::::::::: ::::: ::: ::  :
DEFX  CATACTCATANGCTGCTAAAACATTANTTTTATTTTGAGAAAAGTCTATTCATGTTCTTG
      2110      2120      2130      2140      2150      2160

2150
DEF4  ----------------------------------GCAG-------GTC---CTA---
                                        ::::       :::    :::
DEFX  GCCCATGGAGTTTTCATTTNATTANTTTATTTATTTTGCAGAGATGGAGTCTCACTATGT
      2170      2180      2190      2200      2210      2220

2160
DEF4  ---------GGTCT--------------------GTTTTTC-----------------
               :::::                    :  : :::
DEFX  TGCTCAAGCTGGTCTCCAACTCCTGGGCTCAAGCGATCTTCCTACTTTGGCCTTTGAAAG
      2230      2240      2250      2260      2270      2280

2170
DEF4  --------------------------------------------------AATCAGGTT
                                                        :::::: ::
DEFX  CGCTGAGATTGCCTGTGTGAGCCATCATGGGGGCTCACTGGCCCACTGATTAATCAGATT
      2290      2300      2310      2320      2330      2340

2180      2190      2200      2210      2220      2230
DEF4  GTTTGTTTTTTGCTATTGA-GTTGTTTGACTTCCTTATGTATTCAGATATTTACCCCTTC
      :::::::::::::::::::: .:::::::  :  :::::  ::::::::::: :::
DEFX  AATTGTTTTTTGCTATTGAANTTGTTTGACTTCCTTGTATATTCGGATATTTACCCATTC
      2350      2360      2370      2380      2390      2400

2240      2250      2260      2270      2280      2290
DEF4  TACCACGTAGGCTTTGCAAACATTTTCTCTCATTTTCTGGGTTGCCGTTTCCCTCAGTTG
      ::  ::::::::  ::::::::  ::::::::: :::::  ::::::  ::::  :::::::::
DEFX  TAACACGTAGGGTTTGCAAATATTTTCTCTCATGTTCTGTGTTGCCTTTTCACTCAGTTG
      2410      2420      2430      2440      2450      2460

2300      2310      2320      2330      2340      2350
DEF4  ATTGTTTCCTTTGCTATGAAGATGCTTTAGCGTTCAATGCAGCCCCGCTTGTCTATTTTC
      ::  ::::::::::::::  ::  ::::::::  ::::::  ::::::::::::::::::::::
DEFX  ATGGTTTCCTTTGCTGTGCAGGTGCTTTAGTGTTCAACGCAGCCCCGCTTGTCTATTTTC
      2470      2480      2490      2500      2510      2520

2360      2370      2380      2390      2400      2410
DEF4  CCATTTGTTTATTGCCTGTGCCTTTGGTGTCATAGCCAAGAAATCATTACTCACGTCAAT
      :  ::::   ::::::::::::   :::::  :::::::::::::::::::  :::  : :::
DEFX  C-ATTT---TATTGCCTGTCCCTTTGATGTCATAGCCAAGAAATAATTGCCCAGATTAAT
      2530      2540      2550      2560      2570      2580
```

FIG. 2E

```
          2420       2430       2440       2450       2460       2470
DEF4  GTCCAAA-GCTTTATCTTTGTATGTGCTTCTCGTAGTTGTATGGTTTCAGGTCTTTTCAA
      ::: :::  :::::::::  :  : ::::: ::::::: :::::::::::::: ::::
DEFX  GTCAAAAAGCTTTATCCCTATATATTCTTCTAGTAGTT-TATGGTTTCAGATCTT-----
          2590       2600       2610       2620       2630

2480       2490       2500       2510       2520       2530
DEF4  GTCTATGTTGAG-TCTTCAATCCATGTTGAGCTGATTTTT-TACATGTTGTGAGAGAAAG
      ::::: :: :::::::::::   ::::: ::::::::: ::   :: : ::: :::
DEFX  -----ATGTTTAGGTCTTCAATCCA--TTGAGTTGATTTTTGTATGTGGTATAAGAAAAA
           2640       2650       2660       2670       2680       2690

2540
DEF4  GACCACGTGTATGCACCT------------------------------------------
      :::::: :::::: ::   :
DEFX  GACCACATGTATACATATCTCAAATTCTAAGGTAGTATATATTAGACACATACAATGTGT
          2700       2710       2720       2730       2740       2750

2550       2560                2570
DEF4  ---------------AGC---AACTCATGAAC----------CTTACA--CAACTCTTT
                     :::   ::  : :: :::          ::: ::  :::::::: :
DEFX  CTATTTACACACATTGAGCTGAAAATAATAAACATATTTTTATCTTTCAATCAACTCTAT
          2760       2770       2780       2790       2800       2810

2580       2590       2600       2610       2620       2630
DEF4  ATCTCTCTCACTGAGCTCATTTCACCTGTACCCTGATAAGGTCATTGTCCTCTTCACTCT
      ::: :::::::::: ::  :::::::::: ::::::  ::::  ::::::::  :: :
DEFX  CTCTATCTCACTGAACTTGTTTCACCTATAGCCTGATGAGGTTGCTGTCCTCTCTACCCC
          2820       2830       2840       2850       2860       2870

2640       2650       2660       2670       2680       2690
DEF4  GGCCCCTACAGGAGACTACTCACCCCATTACCTCAGTCGCCCCTTCATGAGGGT-ATAAT
      ::  :::: :::::::::: :::: :::  :  :::::: ::::::::::::: :::::
DEFX  AGCTCCTATAGGAGACTGCTCATCCCCTAACCTCAAAAACCCCTTCATGAGGGTGATAAT
          2880       2890       2900       2910       2920       2930

2700       2710       2720       2730       2740       2750
DEF4  GACCTAGAAGCCTGCAATGAGTTACT-CTCTACTCCACCGGAATTCAGGTCTGGCACCAG
      :  ::: :::  :::::::::  ::: : :::::::  ::  :::::::::::::  : ::
DEFX  GCCCTTGAATCCTGCAATGAATTAGTTCTCTACTACAGTGGAATTCAGGTCTGTTATGAG
          2940       2950       2960       2970       2980       2990

2760       2770       2780       2790       2800       2810
DEF4  TGTTTAGACCT--GAAGAGAATAGTAGGGCCCATTATCAGGAAATAAGAGGCATTTGCTC
      :: : :: ::::  :::::::  : : :: : ::::::::: :::::::::  ::  ::
DEFX  GGTCTGGATCTCTGAAGAGAAGAG---CTCTCATTTTCAGAAAATAAGCAGGATTTATTC
          3000       3010       3020       3030       3040

2820       2830       2840       2850       2860       2870
DEF4  TCTTAAATTATTGAATGAAAGCACTGTTTCCATT-CTTTTTAGAATATTAAAGATTTAAC
       :: :::::: ::::: ::: :::::::::: :::::::::::: ::: ::::::::::
DEFX  CCTGAAATTACTGAATTAAATCACTGTTTCGATTACTTTTTGCAATATTAAA--------
          3050       3060       3070       3080       3090
```

FIG. 2F

```
              2880      2890      2900      2910      2920      2930
DEF4    CAGGAAATATTAGGTATTTCCTGAAAACAGGAAAAAATGCCAGGGTCCTCATCATCACCA
        :: :::::::      :         : :::::::  :::  ::::    ::::::::: :::::::::
DEFX    -AGTAAATATTTA--AACAGGTAAAAACAG-AAATAATGGTAGGGTCCTTATCATCACCG
              3100      3110      3120      3130      3140      3150

2940      2950      2960      2970      2980
DEF4    TCAACTTCAACCTAGGCACAGACACTAAACATAGAGCTTC---CTGTGAAGAAAGCTGGG
        : :: : :::  ::::  ::  :::::::::::   :::::  :::   ::   :::::::::::
DEFX    TGAATTCCAAGCTAG-CATAGACACTAAACCTAGAGATTCACACTAGAATGAAAGCTGGG
              3160      3170      3180      3190      3200      3210

2990      3000      3010      3020      3030      3040
DEF4    AGAGCAGAGGAGGCATTCCAGGGATGTCAAGGCCAATAGGAGTCGGCATCCTCTCTAACA
        :::::::::::::  :  :       : :::::: :::::::::: :   :::  :::::::  :::
DEFX    AGAGCAGAGGAGTC-TCAGAAGGATGTGGAGGCCAATGGACACCTGCAACCTCTCCAACG
              3220      3230      3240      3250      3260      3270

3050      3060      3070      3080      3090      3100
DEF4    AAATGCACACCTCCTCTCACTCAGAAGGCCAAAGGTTTCTTATCTCTGTGCCTTCTCCCA
        :::::  :::::::::::::       ::   ::  :  : :  : : :::::::: ::::::::: ::
DEFX    AAATGCCTACCTCCTCTCACT------GC---AGCATCC--ATCTCTGAGCCTTCTCGCA
              3280      3290             3300       3310      3320

3110      3120      3130      3140      3150      3160
DEF4    GAA-AGCTATAAATCCAAGCTGGCTTCTCCCTCCCCACACAGCTGCTCCTGCTCTCCCTC
        :  : :::::::::::: ::    :::::: ::::  : ::::::::: :    ::::::::::::
DEFX    GCAGAGCTATAAATTCAGCCTGGCTCCTCCGTTCCCACACATCCACTCCTGCTCTCCCTC
              3330      3340      3350      3360      3370      3380

<-------------------------- exon2 ----------
         3170      3180      3190      3200      3210      3220
DEF4    CTC-----CAGGTCACCCCAGCCATGAGGATTATCGCCCTCCTCGCTGCTATTCTCTTGG
        :::      :::::::: :::  :::::::: ::     ::::::::  ::::  ::::: :::
DEFX    CTCTCCTCCAGGTGACTACAGTTATGAGGACCCTCACCCTCCTCTCTGCCTTTCTCCTGG
              3390      3400      3410      3420      3430      3440

-----------------------------------------------------------
         3230      3240      3250      3260      3270      3280
DEF4    TAGCCCTCCAGGTCCGGGCAGGCCCACTCCAGGCAAGAGGTGATGAGGCTCCAGGCCAGG
        : ::::: ::::  :::::::::  :: :::::::::::: ::::: :    ::::  ::::  ::::
DEFX    TGGCCCTTCAGGCCTGGGCAGAGCCGCTCCAGGCAAGAGCTCATGAGATGCCAGCCCAGA
              3450      3460      3470      3480      3490      3500

-----------------------------------------------------------
         3290      3300      3310      3320      3330      3340
DEF4    AGCAGCGTGGGCCAGAAGACCAGGACATATCTATTTCCTTTGCATGGGATAAAAGCTCTG
        ::::::: :     ::::  :::::::::  :      ::::  ::::: ::  ::: :  ::::
DEFX    AGCAGCCTCCAGCAGATGACCAGGATGTGGTCATTTACTTTTCAGGAGATGACAGCTGCT
              3510      3520      3530      3540      3550      3560
```

FIG. 2G

```
              -------------->
         3350      3360      3370      3380      3390      3400
DEF4   CTCTTCAGGTTTCAGGTGAGAGAGGCCAGCATAAAAAAGCTACCGAGTCTAGAGAGACGG
       :::::::::::  :::::::::::  :::::::  : : ::::: :: ::::: ::: ::
DEFX   CTCTTCAGGTTCCAGGTGAGAGATGCCAGCATGCAGA-GCTAC--AGACTAGACAGAAGG
         3570      3580      3590      3600      3610

3410      3420      3430      3440      3450      3460
DEF4   ATGGGAGATGGGCTCTGGAATCACATCTCAATGGTGGATGTCACTTAGGTGGCTTTACTT
       :    :::::  ::::::::::::  :::::  :::  ::::::::::::::::  :::::
DEFX   ACAGGAGACAGGCTCTGGAATTGGATCTCAGTGGCAGATGTCACTTAGGTGGCTATACTT
         3620      3630      3640      3650      3660      3670

3470      3480      3490      3500      3510      3520
DEF4   ACCATCTCTGGGCCTCGATTTTCTTATCTCGAAACTGAATAGAGAGACAAACAAATGTAA
       : ::::::::: ::: :::::::::: :: :: ::: :::::::::: :::: :::: :::
DEFX   AACATCTCTGGTCCTGGATTTTCTCATATCTAAATGGAATAGAGAACCAAAGAAATCTAA
         3680      3690      3700      3710      3720      3730

3530      3540      3550      3560      3570      3580
DEF4   GT-AGTCTTCTTTCTCCAAAGACTTGATTCCAAGGTATGTCTATAAAATTCGCTAGGGTT
       :  : : :::::::::::::::: :::::::::::: ::: : : :::::: ::::  ::
DEFX   GAGATTTTTCTTTCTCCAAAAACTTGATTCCAAGATATGACTGTGAAATTCACTAGATTT
         3740      3750      3760      3770      3780      3790

3590      3600      3610      3620      3630
DEF4   AAGATATGGAGAGACAGATTGACCAGTTCTTTCTGGATCTAAACAAGTA-GAT--ATTAT
       :::::::   ::::   :    : :::::  ::::::::   :  : : ::    : :::
DEFX   AAGATATAAGGAGATG--CTACCTAGTTCCTTCTGGAGCCAGACAAACAAGCTTAAGTAT
         3800      3810      3820      3830      3840      3850

3640      3650      3660      3670      3680      3690
DEF4   AG-GGAAAATATTTCATTCTGCCAACAAAGGAAATTTTAAAAACTGGAGATGGGCTTAAG
       :  :::::::::::::  : :::  : : :::::::: :::::: ::::::: :: ::::
DEFX   ATAGGAAAATATTTCACCCTGTCTATATAGGAGGTTTTAGAACCTGGAGAGGAGCCTAAG
         3860      3870      3880      3890      3900      3910

3700      3710      3720      3730      3740      3750
DEF4   AGTATGTTCAGGTGTGTGTCTGATGGGGCA--AAAGCACACAAATCAGAGCAAAAGAGAA
       : : ::::::::::::::: ::::::: ::  :: ::: : :: : ::::::: :::::
DEFX   AATGTGTTCAGGTGTGTGTGTGATGGG-CAGGAATGCAGAAAAGTGA-AGCAAAGGAGAA
         3920      3930      3940      3950      3960      3970

3760      3770      3780      3790      3800      3810
DEF4   TGAGTCTCAAATCCTGTATGAGCAGCATTGCTCTGTGTATTTATTCCTATTGACTAAGGT
       :::::::: ::::::::: ::  ::::: ::::::::::::::::::::::::::  : :
DEFX   TGAGTCTCGAATCCTGTGTGACCAGCACTGCTCTGTGTATTTATTCCTATTGACTGAGAT
         3980      3990      4000      4010      4020      4030

3820    3830      3840      3850      3860      3870
DEF4   TGTTTGTGCTACCGGCACTAATGCAGCCAGCATCACCGGTCAGCCAGCATGTGCATTCTC
       ::::::::::::::::: :::: :::::: :::::: ::::::: :::::::: ::::::
DEFX   TGTTTGTGCTACCGGCTGTAATACAGCCAACATCACTCATCAGCCAACATGTGACTTCTC
         4040      4050      4060      4070      4080      4090
```

FIG. 2H

```
          3880      3890      3900      3910      3920      3930
DEF4  CAAGATTCCCTTTACCACCCACCGCTGACCTTGGTGCTTAATTTCTCAGTCTTCCTCTGT
      ::::::::::::::::::::::    :     ::  ::  :  :::::  :   ::   :::::
DEFX  CAAGATTCCCTTTACCACCCACTGCTGNACCCCGTACTCAGTTTCTGATGCTCTCTCTGG
          4100      4110      4120      4130      4140      4150

<--------------- exon3 --------------------------
          3940      3950      3960      3970      3980      3990
DEF4  GTTCCCAGGCTCAACAAGGGGCATGGTCTGCTCTTGCAGATTAGTATTCTGCCGGCGAAC
      ::  :::::::::::: :::::  ::  ::::::  ::::::::: ::  :::  ::::
DEFX  GTCCCCAGGCTCAACAAAGGGCTTGATCTGCCATTGCAGAGTACTATACTGCATTTTTGG
          4160      4170      4180      4190      4200      4210

------------------------ exon3 --------------------------
          4000      4010      4020      4030      4040      4050
DEF4  AGAACTTCGTGTTGGGAACTGCCTCATTGGTGGTGTGAGTTTCACATACTGCTGCACGCG
      :::::  ::  :::::  ::::  ::::  ::::       :::::   :  :  :: :::::::
DEFX  AGAACATCTTGGTGGGACCTGCTTCATCCTTGGTGAACGCTACCCAATCTGCTGCT----
          4220      4230      4240      4250      4260      4270

------------------------ exon3 --------------------------
          4060      4070      4080      4090      4100      4110
DEF4  TGTCGATTAACATTCTGCTGTCCAAGAGAATGTCATGCTGGGAACGCCATCATCGGTGGT
           :  :::
DEFX  -----ACTAA--------------------------------------------------

------------------------ exon3 --------------------------
          4120      4130      4140      4150      4160      4170
DEF4  GTTAGCTTCACATGCTTCTGCAGCTGAGCTTGCAGAATAGAGAAAAATGAGCTCATAATT
                                 :::::::::  :::::::::  :::  ::::::::
DEFX  ------------------------GCTTGCAGACTAGAGAAAAA-GAGTTCATAATT
                                        4280      4290      4300

------------------------ exon3 --------------------------
          4180      4190      4200      4210      4220      4230
DEF4  TGCTTTGAGAGCTACAGGAAATGGTTGTTTCTCCTATACTTTGTCCTTAACATCTT-TCT
      :  ::::::::  ::  :::  :::  :::  ::  :  :::::  :::::::::  ::  :  :::
DEFX  TTCTTTGAGCATTAAAGGGAATTGTTATT---CTTATACCTTGTCCTCGATTTCCTGTCC
         4310      4320      4330      4340      4350      4360

Poly Ad
      --------------->
          4240      4250      4260      4270      4280      4290
DEF4  TGATCCTAAATATATATCTCGTAACAAGATGTCTTTGTTTACACCTCTTTGAAATTTGAT
      :  ::::  :::::  :::    :  :::::::  :::  ::      ::::
DEFX  TCATCCCAAATAAATACTTGGTAACATGATTTCCGGGTTTTTTTTTTTTT
          4370      4380      4390      4400      4410
```

FIG. 2I

```
            10         20         30         40         50         60
DEF4  GTCTGCCCTCTCTGCTCGCCCTGCCTAGCTTGAGGATCTGTCACCCCAGCCATGAGGATT
      :::::::  :::::   :  :::     :  :::::::  :  :::::: ::   :::   :::::::
DEFX  CTCTGCCCACTCTGGTAGCCTCACGTAGCTTAACAATCTGTGACTACAGTTATGAGGACC
            10         20         30         40         50         60

70         80         90        100        110        120
DEF4  ATCGCCCTCCTCGCTGCTATTCTCTTGGTAGCCCTCCAGGTCCGGGCAGGCCCACTCCAG
      ::   :::::::::   ::::     :::::  ::::   :::::  ::    :::::::   ::  ::::::
DEFX  CTCACCCTCCTCTCTGCCTTTCTCCTGGTGGCCCTTCAGGCCTGGGCAGAGCCGCTCCAG
            70         80         90        100        110        120

130        140        150        160        170        180
DEF4  GCAAGAGGTGATGAGGCTCCAGGCCAGGAGCAGCGTGGGCCAGAAGACCAGGACATATCT
      :::::::  : :::::    ::::  ::::  ::::::: :       ::::  :::::::::: :
DEFX  GCAAGAGCTCATGAGATGCCAGCCCAGAAGCAGCCTCCAGCAGATGACCAGGATGTGGTC
           130        140        150        160        170        180

190        200        210        220        230        240
DEF4  ATTTCCTTTGCATGGGATAAAAGCTCTGCTCTTCAGGTTTCAGGCTCAACAAGGGGCATG
      ::::  ::::  ::  :  :::  :  ::::    ::::::::::::  ::::::::::::::  ::::  ::
DEFX  ATTTACTTTTCAGGAGATGACAGCTGCTCTCTTCAGGTTCCAGGCTCAACAAAGGGCTTG
           190        200        210        220        230        240

250        260        270        280        290        300
DEF4  GTCTGCTCTTGCAGATTAGTATTCTGCCGGCGAACAGAACTTCGTGTTGGGAACTGCCTC
      :::::   :::::::: ::  :::  ::::          :::::  ::  :: ::::: ::::  ::
DEFX  ATCTGCCATTGCAGAGTACTATACTGCATTTTTGGAGAACATCTTGGTGGGACCTGCTTC
           250        260        270        280        290        300

310        320        330        340        350        360
DEF4  ATTGGTGGTGTGAGTTTCACATACTGCTGCACGCGTGTCGATTAACGTTCTGCTGTCCAA
      ::   :::::    :   :  : ::   ::::::            :  :  :::
DEFX  ATCCTTGGTGAACGCTACCCAATCTGCTG---------CTACTAA---------------
           310        320                   330        340        350

370        380        390        400        410        420
DEF4  GAGAATGTCATGCTGGGAACGCCATCATCGGTGGTGTTAGCTTCACATGCTTCTGCAGCT

DEFX  ------------------------------------------------------------
                360        370        380                      390

430        440        450        460        470        480
DEF4  GAGCTTGCAGAATAGAGAAAAATGAGCTCATAATTTGCTTTGAGAGCTACAGGAAATGGT
        ..:::::::::: :::::::::::::  :::  ::::::::::: :::::::    ::  :::   :::
DEFX  --GCTTGCAGACTAGAGAAAAA-GAGTTCATAATTTTCTTTGAGCATTAAAGGGAAT---
            400        410        420        430        440        450

490        500        510        520        530
DEF4  TGTTTCTCCTATACTTTGTCCTTAACATCTT-TCTTGATCCTAAATATATATCTCGTAAC
      ::::   ::  :::::  :::::::::   :   ::  :  ::  :::: ::::: :::   :  :::::
DEFX  TGTTATTCTTATACCTTGTCCTCGATTTCCTGTCCTCATCCCAAATAAATACTTGGTAAC
           460        470        480        490        500        510

540
DEF4  AAG
      : :
DEFX  ATG
```

FIG. 3

```
<--------------- Signal peptide ------------------><--
        5              10             15            20
MetArgThrLeuThr LeuLeuSerAlaPhe LeuLeuValAlaLeu GlnAlaTrpAlaGlu ----------------- Propiece ---------------------
         25             30             35            40
ProLeuGlnAlaArg AlaHisGluMetPro AlaGlnLysGlnPro ProAlaAspAspGln ----------------- Propiece ---------------------
         45             50             55            60
AspValValIleTyr PheSerGlyAspAsp SerCysSerLeuGln ValProGlySerThr --------><---------- Mature peptide ----------------------
         65             70             75            80
LysGlyLeuIleCys HisCysArgValLeu TyrCysIlePheGly GluHisLeuGlyGly ----------------- Mature peptide ----->
         85             90         94
ThrCysPheIleLeu GlyGluArgTyrPro IleCysCysTyr
```

FIG. 4

```
                    SIGNAL                    PROPIECE
DEF4_HUMAN   MRIIALLAAILLVALQVRA   GPLQAR-------GDEAPGQ-EQRGPEDQDISISFAWDKSS
DEF5_HUMAN   MRTIAILAAILLVALQAQA   ESLQER-------ADEATTQ-KQSGEDNQDLAISFAGNGLS
DEF6_HUMAN   MRTLTILTAVLLVALQAKA   EPLQAEDDPLQAKAYEADAQ-EQRGANDQDFAVSFAEDASS
DEF1_HUMAN   MRTLAILAAILLVALQAQA   EPLQAEDDPLQAKAYEADAQ-EQRGANDQDFAVSFAEDASS
DEFX         MRTLTLLSAFLLVALQAWA   EPLQAR-------AHEMPAQ-KQPPADDQDVVIYFSGDDSC
             **...*.*  ******  *   **                *         *     .  . .

PROPIECE    Mature PEPTIDE
DEF4_HUMAN   ALQVSGSTRGM   VCSCRLVFCRRTELRVGNCLIGGVSFTYCCTRVD
DEF5_HUMAN   ALRTSGSQARA   TCYCRTGRCATRESLSGVCEISGRLYRLCCR---
DEF6_HUMAN   SLRALGSTRAF   TCHCRR-SCYSTEYSYGTCTVMGINHRFCCL---
DEF1_HUMAN   APKHPGSRKNM   ACYCRIPACIAGERRYGTCIYQGRLWAFCC----
DEFX         SLQVPGSTKGL   ICHCRVLYCIFGEHLGGTCFILGERYPICCY---
             . .  **        *  **   *    *    *   *     **
                           ^ ^        ^          ^         ^^
```

FIG. 5

SEQUENCE LISTING (1) GENERAL INFORMATION:

(iii) NUMBER OF SEQUENCES: 6

(2) INFORMATION FOR SEQ ID NO: 1:

(i) SEQUENCE CHARACTERISTICS:
       (A) LENGTH: 4415 BASE PAIRS
       (B) TYPE: NUCLEOTIDE
       (C) STRANDEDNESS: DOUBLE
       (D) TOPOLOGY: LINEAR (ii) MOLECULE TYPE: DNA (vi) ORIGINAL SOURCE:
       (A) ORGANISM: Homo sapiens (ix) FEATURE:
       (A) NAME/KEY:  Exon 1
       (B) LOCATION: 1836..1874

(ix) FEATURE:
       (A) NAME/KEY:  Exon 2
       (B) LOCATION: 3394..3577

(ix) FEATURE:
       (A) NAME/KEY:  Exon 3
       (B) LOCATION: 4161..4380

(ix) FEATURE:
       (A) NAME/KEY:  start CDS
       (B) LOCATION: 3406..3408

(ix) FEATURE:
       (A) NAME/KEY:  stop CDS
       (B) LOCATION: 4276..4278

(ix) FEATURE:
       (A) NAME/KEY: polyadenylation site
       (B) LOCATION: 4374..4379

(xi) SEQUENCE DESCRIPTION: SEQ ID NO: 1:

```
ACACCATTTG TCTTCATGTA ACCCCATTAG CTATACCCTC TAGTGCAAGG AAACCATAGG      60

GCCTAGGTCA CACCATGAGG CTGCNCTTAC AAGTTATGCA AAAACTATGG ACTTGGGAGA     120

CCTGTGCGTA ACAACATCAC ACNCCAAATT TAACCAGCTC TCCCCATAAC AGCACGCTCA     180

TGTGTTACTG AGGAAATGCC TGTGGATTGG AGTGTGTTCT GTGTGCAGGA GGCTGGTCCA     240

GGTTTCACTT CTGCAGGACA CTGGACGTTT CCCAAAACCA GCAGACTTTC CCCACGTGCA     300

CACACACCCC TTCTCATTTT GCCTCTACAT CCATATCCAC TGGGCCCTTC AGGCACCTAC     360

TAATGCCCTA GAACCTAAAA CCATCATCTG GGGCCCAGTT CCCTGAATGG CCCTAATCTC     420

TTCCTCTGCT GGAATGAGTC CAGTGCCCAC TTCCTCCAAC GGTGAAATTG CTGGGCTGCT     480

ACAGATCAGG AACTCACTGC TTCCTCATAG GGGCAGCCGA CTTCACTGCT CTGCAACAGC     540

GACCACCCCT AGCGAGGCTT GAGATGCCTC TTGCCTCCTT AAGACTGAGG GAGACGCTTC     600

AGCTCTCACT CCACTGCCCC AAGTCCTCCA CAGCGCGGTG CCTGCTGCCT TCACACAGAG     660

CTGCAGGGGN AGGTCCTGTG TATCCGGCCT GCTGGACCAG CGCTGTGCAC AACCCTCCCA     720

TGGCAACAGT GGCTGCCCGG CCTGCACACT GGGCTTGGCA ACCTCGCTGT AGGTATTTAT     780

TCCCTCAGGA GTGACTGCAT TCTTTTCCCA TTTCCAGAAA ACTGATGCCA TTTACCTCAC     840

TATGAGGAGG AGGAGGAGGA GGAGGGTGGA GAGTGGTACA TTTTAAAATG TGCACTATTC     900

TCCCTAGGAC TCCCCCTCAA ATAACCCAGG AGGGACCATA CCAGCTCATT CCTGTGTATC     960
```

```
CCAAGCATAN GAGTAATCAT CCCACTCATG CTGAGTGTAT GGTGGCCATT AAGCCTGCCC    1020

TGAACTGGCT TTAGAACAAG GTGTTTGAGC ACACAGCACC GTCTTGCTGC CACCTTGGCC    1080

CCCTCCCTTG TGAGACCTCT GAGACACATT NAGGTCTCAC CTAAAAATCT CAGGATTTCT    1140

AGGCCCAAAN CGGTCCTAAA AAATTGTTCA GTCTGAACTC TCTAAGGTCA AGAGAAGAGG    1200

TGGTTGCTCC CTCTAAGAAA CCACATGTTG CATGTACATC CTTAATTCCG GAAAGTCCAA    1260

CAAACCTGCC CTGCTTAGCA ACACAAGCCG AGGTGGTACT CCTCTCACCC GGGCATTCTC    1320

CAACACACCT GTTTGTCCAA ACAGCTTTGA TTTGTTTTTA TAGTTGGACC CCAGGTTCCC    1380

AGGAGGCTGG TTCAGGCCAT ATTCCAAATC CTCATCTGTG TGTGAGTGGC ATTCTTAGCC    1440

TAGCCTCCTT ACAGGGTGGA TACTATGATA CACAGCCAGG CTGTCCCAGT GGCTTTCAAT    1500

ATTCTTTTGG TCCAGATAGT TCAGCCTCAG CACCAGTGTA GGCATCACAG GGTCAATTGT    1560

CTTAGGAGTC ATGGAGAATT CATAGTTGGT AGCTACCTGG GCCTGGCCAG GGCTGACCAT    1620

AGACAAGGCA TCCCTCTGTG AACTCCTATT TTAATGCCAG CTTCCCAACA AATTTCTCAA    1680

CTGCTCTTAC CAGCAGGTAT TTAAACTACT CAATAGAAAG TAACCCTGAA AATTAGGACA    1740

CCTGTTCCCA AAAGACCCTT AAATAGGGGA AGTCCTTTCN CTGCTTGTGC ACAGCTGCTG    1800

ATGTGGCAAC ATGAGGCCTG GGACAGGGGA CTGTCCTCTG CCCACTCTGG TAGCCTCACG    1860

TAGCTTAACA ATCTGTCAGT AATACAATAC AAAACTTAAA CTTTCATACT GCGGTTCCAC    1920

CCAGGAAGCT GTGTTCCCAA TCTGACCCGT GATTATGGGG CCACCTCAGA GGGNACCCAG    1980

TGAGGGAATA TTTTGCCATC TGGGACTGTT GGTTGCTGGG GGCAGTGGCT ATGAGCTCAG    2040

TTAATAAACT CAAGCAGTTT CCTTCCAAAC ACACATGTCC TACTTAACGT GTCCAACAGA    2100

GATGATCATA CTCATANGCT GCTAAAACAT TANTTTTATT TTGAGAAAAG TCTATTCATG    2160

TTCTTGGCCC ATGGAGTTTT CATTTNATTA NTTTATTTAT TTTGCAGAGA TGGAGTCTCA    2220

CTATGTTGCT CAAGCTGGTC TCCAACTCCT GGGCTCAAGC GATCTTCCTA CTTTGGCCTT    2280

TGAAAGCGCT GAGATTGCCT GTGTGAGCCA TCATGGGGGC TCACTGGCCC ACTGATTAAT    2340

CAGATTAATT GTTTTTTGCT ATTGAANTTG TTTGACTTCC TTGTATATTC GGATATTTAC    2400

CCATTCTAAC ACGTAGGGTT TGCAAATATT TTCTCTCATG TTCTGTGTTG CCTTTTCACT    2460

CAGTTGATGG TTTCCTTTGC TGTGCAGGTG CTTTAGTGTT CAACGCAGCC CCGCTTGTCT    2520

ATTTTCCATT TTATTGCCTG TCCCTTTGAT GTCATAGCCA AGAAATAATT GCCCAGATTA    2580

ATGTCAAAAA GCTTTATCCC TATATATTCT TCTAGTAGTT TATGGTTTCA GATCTTATGT    2640

TTAGGTCTTC AATCCATTGA GTTGATTTTT GTATGTGGTA TAAGAAAAAA GACCACATGT    2700

ATACATATCT CAAATTCTAA GGTAGTATAT ATTAGACACA TACAATGTGT CTATTTACAC    2760

ACATTGAGCT GAAAATAATA AACATATTTT TATCTTTCAA TCAACTCTAT CTCTATCTCA    2820

CTGAACTTGT TTCACCTATA GCCTGATGAG GTTGCTGTCC TCTCTACCCC AGCTCCTATA    2880

GGAGACTGCT CATCCCCTAA CCTCAAAAAC CCCTTCATGA GGGTGATAAT GCCCTTGAAT    2940

CCTGCAATGA ATTAGTTCTC TACTACAGTG GAATTCAGGT CTGTTATGAG GGTCTGGATC    3000

TCTGAAGAGA AGAGCTCTCA TTTTCAGAAA ATAAGCAGGA TTTATTCCCT GAAATTACTG    3060

AATTAAATCA CTGTTTCGAT TACTTTTTGC AATATTAAAA GTAAATATTT AAACAGGTAA    3120

AAACAGAAAT AATGGTAGGG TCCTTATCAT CACCGTGAAT TCCAAGCTAG CATAGACACT    3180

AAACCTAGAG ATTCACACTA GAATGAAAGC TGGGAGAGCA GAGGAGTCTC AGAAGGATGT    3240

GGAGGCCAAT GGACACCTGC AACCTCTCCA ACGAAATGCC TACCTCCTCT CACTGCAGCA    3300

TCCATCTCTG AGCCTTCTCG CAGCAGAGCT ATAAATTCAG CCTGGCTCCT CCGTTCCCAC    3360
```

```
ACATCCACTC CTGCTCTCCC TCCTCTCCTC CAGGTGACTA CAGTTATGAG GACCCTCACC    3420

CTCCTCTCTG CCTTTCTCCT GGTGGCCCTT CAGGCCTGGG CAGAGCCGCT CCAGGCAAGA    3480

GCTCATGAGA TGCCAGCCCA GAAGCAGCCT CCAGCAGATG ACCAGGATGT GGTCATTTAC    3540

TTTTCAGGAG ATGACAGCTG CTCTCTTCAG GTTCCAGGTG AGAGATGCCA GCATGCAGAG    3600

CTACAGACTA GACAGAAGGA CAGGAGACAG GCTCTGGAAT TGGATCTCAG TGGCAGATGT    3660

CACTTAGGTG GCTATACTTA ACATCTCTGG TCCTGGATTT TCTCATATCT AAATGGAATA    3720

GAGAACCAAA GAAATCTAAG AGATTTTTCT TTCTCCAAAA ACTTGATTCC AAGATATGAC    3780

TGTGAAATTC ACTAGATTTA AGATATAAGG AGATGCTACC TAGTTCCTTC TGGAGCCAGA    3840

CAAACAAGCT TAAGTATATA GGAAAATATT TCACCCTGTC TATATAGGAG GTTTTAGAAC    3900

CTGGAGAGGA GCCTAAGAAT GTGTTCAGGT GTGTGTGTGA TGGGCAGGAA TGCAGAAAAG    3960

TGAAGCAAAG GAGAATGAGT CTCGAATCCT GTGTGACCAG CACTGCTCTG TGTATTTATT    4020

CCTATTGACT GAGATTGTTT GTGCTACCGG CTGTAATACA GCCAACATCA CTCATCAGCC    4080

AACATGTGAC TTCTCCAAGA TTCCCTTTAC CACCCACTGC TGNACCCCGT ACTCAGTTTC    4140

TGATGCTCTC TCTGGGTCCC CAGGCTCAAC AAAGGGCTTG ATCTGCCATT GCAGAGTACT    4200

ATACTGCATT TTTGGAGAAC ATCTTGGTGG ACCTGCTTCA ATCCTTGGTG AACGCTACCC    4260

AATCTGCTGC TACTAAGCTT GCAGACTAGA GAAAAGAGT TCATAATTTT CTTTGAGCAT    4320

TAAAGGGAAT TGTTATTCTT ATACCTTGTC CTCGATTTCC TGTCCTCATC CCAAATAAAT    4380

ACTTGGTAAC ATGATTTCCG GGTTTTTTTT TTTTT                              4415

(2) INFORMATION FOR SEQ ID NO: 2:

(i) SEQUENCE CHARACTERISTICS:
        (A) LENGTH: 453 BASE PAIRS
        (B) TYPE: NUCLEOTIDE
        (C) STRANDEDNESS: DOUBLE
        (D) TOPOLOGY: LINEAR (ii) MOLECULE TYPE: cDNA (vi) ORIGINAL SOURCE:
         (A) ORGANISM: Homo sapiens (xi) SEQUENCE DESCRIPTION: SEQ ID NO: 2:

CTCTGCCCAC TCTGGTAGCC TCACGTAGCT TAACAATCTG TGACTACAGT T ATG AGG       57
                                                         Met Arg
                                                           1

ACC CTC ACC CTC CTC TCT GCC TTT CTC CTG GTG GCC CTT CAG GCC TGG      105
Thr Leu Thr Leu Leu Ser Ala Phe Leu Leu Val Ala Leu Gln Ala Trp
        5                  10                 15

GCA GAG CCG CTC CAG GCA AGA GCT CAT GAG ATG CCA GCC CAG AAG CAG      153
Ala Glu Pro Leu Gln Ala Arg Ala His Glu Met Pro Ala Gln Lys Gln
 20                  25                  30

CCT CCA GCA GAT GAC CAG GAT GTG GTC ATT TAC TTT TCA GGA GAT GAC      201
Pro Pro Ala Asp Asp Gln Asp Val Val Ile Tyr Phe Ser Gly Asp Asp
 35                  40                  45                  50

AGC TGC TCT CTT CAG GTT CCA GGC TCA ACA AAG GGC TTG ATC TGC CAT      249
Ser Cys Ser Leu Gln Val Pro Gly Ser Thr Lys Gly Leu Ile Cys His
                  55                  60                  65

TGC AGA GTA CTA TAC TGC ATT TTT GGA GAA CAT CTT GGT GGG ACC TGC      297
Cys Arg Val Leu Tyr Cys Ile Phe Gly Glu His Leu Gly Gly Thr Cys
             70                  75                  80

TTC ATC CTT GGT GAA CGC TAC CCA ATC TGC TGC TAC TAA GCTTGCAGAC       346
Phe Ile Leu Gly Glu Arg Tyr Pro Ile Cys Cys Tyr  *
```

```
                    85              90              95
TAGAGAAAAA GAGTTCATAA TTTTCTTTGA GCATTAAAGG GAATTGTTAT TCTTATACCT    406

TGTCCTCGAT TTCCTGTCCT CATCCCAAAT AAATACTTGG TAACATG                  453
```

(2) INFORMATION FOR SEQ ID NO: 3:

(i) SEQUENCE CHARACTERISTICS:
        (A) LENGTH: 94 AMINO ACIDS
        (B) TYPE: AMINO ACID
        (C) STRANDEDNESS: SINGLE
        (D) TOPOLOGY: LINEAR (ii) MOLECULE TYPE: PROTEIN (vi) ORIGINAL SOURCE:
        (A) ORGANISM: Homo sapiens (ix) FEATURE:
        (A) NAME/KEY: SIGNAL PEPTIDE
        (B) LOCATION: 1..19

(ix) FEATURE:
        (A) NAME/KEY: PRO REGION
        (B) LOCATION: 20..63

(ix) FEATURE:
        (A) NAME/KEY: MATURE PEPTIDE
        (B) LOCATION: 64..94

(xi) SEQUENCE DESCRIPTION: SEQ ID NO: 3:

```
Met Arg Thr Leu Thr Leu Leu Ser Ala Phe Leu Leu Val Ala Leu Gln
1               5                   10                  15

Ala Trp Ala Glu Pro Leu Gln Ala Arg Ala His Glu Met Pro Ala Gln
            20                  25                  30

Lys Gln Pro Pro Ala Asp Asp Gln Asp Val Val Ile Tyr Phe Ser Gly
        35                  40                  45

Asp Asp Ser Cys Ser Leu Gln Val Pro Gly Ser Thr Lys Gly Leu Ile
    50                  55                  60

Cys His Cys Arg Val Leu Tyr Cys Ile Phe Gly Glu His Leu Gly Gly
65                  70                  75                  80

Thr Cys Phe Ile Leu Gly Glu Arg Tyr Pro Ile Cys Cys Tyr
                85                  90
```

(2) INFORMATION FOR SEQ ID NO: 4:

(i) SEQUENCE CHARACTERISTICS:
        (A) LENGTH: 19 AMINO ACIDS
        (B) TYPE: AMINO ACID
        (C) STRANDEDNESS: SINGLE
        (D) TOPOLOGY: LINEAR (ii) MOLECULE TYPE: SIGNAL PEPTIDE (vi) ORIGINAL SOURCE:
        (A) ORGANISM: Homo sapiens (xi) SEQUENCE DESCRIPTION: SEQ ID NO: 4:

```
Met Arg Thr Leu Thr Leu Leu Ser Ala Phe Leu Leu Val Ala Leu Gln
1               5                   10                  15

Ala Trp Ala
```

(2) INFORMATION FOR SEQ ID NO: 5:

(i) SEQUENCE CHARACTERISTICS:
        (A) LENGTH: 44 AMINO ACIDS
        (B) TYPE: AMINO ACID

```
            (C) STRANDEDNESS: SINGLE
            (D) TOPOLOGY: LINEAR (ii) MOLECULE TYPE: PRO REGION (vi) ORIGINAL SOURCE:
         (A) ORGANISM: Homo sapiens (xi) SEQUENCE DESCRIPTION: SEQ ID NO: 5:

Glu Pro Leu Gln Ala Arg Ala His Glu Met Pro Ala Gln Lys Gln Pro
1               5                   10                  15

Pro Ala Asp Asp Gln Asp Val Val Ile Tyr Phe Ser Gly Asp Asp Ser
            20                  25                  30

Cys Ser Leu Gln Val Pro Gly Ser Thr Lys Gly Leu
        35                  40

(2) INFORMATION FOR SEQ ID NO: 6:

(i) SEQUENCE CHARACTERISTICS:
         (A) LENGTH: 31 AMINO ACIDS
         (B) TYPE: AMINO ACID
         (C) STRANDEDNESS: SINGLE
         (D) TOPOLOGY: LINEAR (ii) MOLECULE TYPE: MATURE PEPTIDE (vi) ORIGINAL SOURCE:
         (A) ORGANISM: Homo sapiens (xi) SEQUENCE DESCRIPTION: SEQ ID NO: 6:

Ile Cys His Cys Arg Val Leu Tyr Cys Ile Phe Gly Glu His Leu Gly
1               5                   10                  15

Gly Thr Cys Phe Ile Leu Gly Glu Arg Tyr Pro Ile Cys Cys Tyr
            20                  25                  30
```

HUMAN DEFENSIN DEF-X

This application claims priority, under 35 U.S.C. § 371, to PCT/FR98/01864.

The present invention relates to a novel human polypeptide defensin Def-X, homologous to HNP-4, its genomic DNA and CDNA.

The invention also relates to cloning and expression vectors, and cells transformed with said vectors. The subject of the invention is also the use of said polypeptides as antibiotic, cytotoxic, repair and endocrine regulatory agent and as pesticide as well as cosmetic or pharmaceutical compositions for the treatment of microbial infections, in particular bacterial, fungal and viral infections, or parasitic infections, cancers, of inflammation and of immune deficiency. Finally, the invention comprises diagnostic methods and kits for the determination of a microbial or parasitic infection and of an inflammation, or for screening for predisposition to immune deficiencies or cancer diseases.

Antimicrobial substances are key elements in the defence of multicellular organisms. Among these substances, there are both simple inorganic compounds (hydrogen peroxide, hypochlorous acid, nitric oxide) and complex proteins and peptides. They are present at the first lines of defence, at the surface of the mucous membranes of various organs, in particular in the epithelial cells of the intestine and of the lungs, depending on the species, as well as in the microbicidal organs of phagocytic cells of hematopoietic origin, where they were first identified. Their synthesis de novo or their release from storage sites—organelles of the lysosome or cytoplasmic granule type which are capable of storing them in an inactive or latent form—can be induced rapidly, which makes them particularly important in the early phases of resistance to infections (Martin et al., 1995).

The antimicrobial proteins of less than one hundred aminoacids in size are arbitrarily called antimicrobial peptides. Several families of antimicrobial peptides have been identified, which differ in the presence within them of disulfide bridges, in their aminoacid composition, their structural conformation and in their activity spectrum. The antimicrobial peptides comprising six conserved cysteines form the defensin family. This family is composed of antimicrobial peptides which are present in numerous species, which are abundant and which are about 3–4 kDa (Ganz and Lehrer, 1994). These peptides are formed of 30 to 40 aminoacids, of which six invariant cysteins which form three intramolecular disulfide linkages. They have complex conformation, are amphipathic, rich in beta antiparallel sheets but lack alpha helices (Lehrer and Ganz, 1992). The antimicrobial action of defensins is thought to result from their insertion into the membranes of the target cells, allowing the formation of voltage-dependent channels. White et al. (1995) describe the possible mechanisms of membrane insertion and of formation of multimeric pores by the defensins, which allow the permeabilization of the membranes of the target cells, for example microbial or tumor cells. The crystallographic structure of human neutrophil defensin HNP-3 (see below) has been determined, and a specific mechanism of dimerization of the human neutrophil defensins is in addition suggested. Increased knowledge of this family of peptides and comparison of their sequences and activity spectra will make it possible to better understand these mechanisms and their specificities, as well as the aminoacid residues more particularly involved in these phenomena.

The defensins are divided into three familities of peptides which are structurally different: the "conventional" defensins, the beta-defensins and the insect defensins. These families exhibit differences as regards the position of and the distance between the conserved cysteine residues, as well as those of other conserved aminoacids (proline, glycine) (Ganz and Lehrer, 1995).

Human defensins, of the conventional type, come essentially from two sources. They were first identified by peptide purification from neutrophil extracts. Four defensins have thus been isolated: "human neutrophil peptides" HNP-1, HNP-2, HNP-3, and HNP-4. The first three are different products of the same gene (Ganz et Lehrer, 1995). These three peptides represent 99% of the defensin content of the neutrophils, whereas HNP-4 is also present therein, but at concentrations which are 100 times lower. More recently, two human enteric defensins, HD-5 and HD-6, were characterized in the small intestine and more precisely in the Paneth cells (Bevins et al., 1996). While 16 enteric defensin genes have been identified in mice, only these two homologs have been identified in humans (Mallow et al., 1996).

Defensins have an antimicrobial action on a broad spectrum of microorganismes in vitro (Martin et al., 1995). This activity spectrum, which is particularly broad, comprises bacteria, Gram-positive and Gram-negative bacteria, several fungi, mycobacteria, parasites including spirochetes and several enveloped viruses including the HSV and HIV viruses. They are also cytotoxic for several categories of normal and malignant cells, including cells resistant to TNF-alpha and to the cytolytic NK factor (Kagan et al., 1994). The large quantity of targets of the defensins and their abundance in blood cells specialized in the immune defence, as well as the dramatic increase in their concentration during severe infections, suggest that these molecules could play an important role in the natural immunity to infections and to cancers. In particular, the increase in the transcription of the defensin genes and the release of cytoplasmic granules containing presynthesized defensins in response to stimuli, contributes to the local antimicrobial response, it being possible for the defensins to participate in the inflammatory reaction, in the repair processes and in endocrine regulation during infection. The hematopoietic defensins could contribute to the phenomenon of lysis of cancer cells, a phenomenon which is mediated by the neutrophils during the antibody-dependent immune response. The precise physiological role of the enteric defensins is not clearly established. They could stem the proliferation of the intraluminal flora or prevent the translocation of bacteria across the intestinal mucosa (Mallow et al., 1996). The abundance of the defensin mRNA in the Paneth cells reinforces the hypothesis that these epithelial cells could play a key role in the immune defence in the intestine. It has moreover been shown that their expression scheme coincides with the appearance of the Paneth cells during embryogenesis. Mallow et al. (1996) have suggested that low levels of expression of enteric defensins in the fetus could be the evidence of an immaturity of a local defence, which would predispose children born prematurely to infections due to intestinal microorganisms.

A defensin concentration corresponding to 10% of the normal level is observed in patients suffering from "specific granule deficiency", a rare disease of the development of the granulocytes. The affected subjects suffer from frequent infections caused by common bacteria (Ganz and Lehrer, 1995).

Biochemically modified defensins are potential prophylactic and therapeutic agents against infections (Ganz and Lehrer, 1995). Research relating to these antimicrobial peptides or other molecules participating in the natural immunity have gained special importance since phenomena of resistance of microorgnisms to traditional antibiotics started to develop (Bevins et al., 1996).

The primary structure of defensins, in particular of human defensins, has been the subject of recent studies (White et al., 1995; Mallow et al., 1996). The conventional defensins comprise 29 to 35 aminoacids, but are derived from precursors—preproteins—comprising 90 to 100 aminoacids. The proteolytic maturation of the human neutrophil defensins to mature peptides is coupled with their despatch to the granulocytes; the function of the propeptide would include the inactivation of the precursor form of defensin and a support for the acquisition of the active conformation of the mature peptide (Martin et al., 1995). The peptide homologies are maximal at the level of the signal peptides, and minimal at the level of the mature peptides, which comprise nevertheless six cysteine residues which are fully conserved. While the conservation of these residues appears to be necessary for the acquisition of secondary structures which are involved in the activity of defensins, the differences in sequences which exist within the very large family of these antimicrobial peptides, in particular at their N-terminal end, but also in other nonconserved regions, appear to be important determinants of their activity spectrum, and of their antimicrobial or cytotoxic efficacy. The identification of novel members of this family of peptides, in particular of human defensins, is therefore necessary for understanding their mechanism of action and their specificity as well as for their use as anti-infectious and/or cytotoxic agents, or for designing variant peptides exhibiting specific spectra and/or of reduced or increased efficacy.

Sparkes et al. (1989) located the gene encoding HNP-1 on chromosome 8, in the 8p23 region. Bevins et al. (1995), and Mallow et al. (1996) Icoated the two genes encoding HD-5 and HD-6 on chromosome 8, more precisely in the 8p21-pter region, a region including the region previously identified as carrying the hematopoietic defensins. The genes encoding the human enteric defensins HD-5 and HD-6 contain two exons, whereas those encoding the hematopoietic defensins contain three of them, the last two exons encoding the prepropeptide, both in humans and in guinea pigs and rabbits (Mallow et al., 1996). Comparison of the genome sequences of the HD-5 and HD-6 genes has revealed a very strong similarity between the noncoding flanking sequences in 5', suggesting that the latter contain the information necessary to the tissue specificity of the expression of these genes; these same regions carry, in addition, many binding sites for transcription factors, including two AP2 sites and six IL6 sites, suggesting pathways for regulating the expression of these genes during inflammatory processes. More generally, the very high degree of similarity between the sequences and the genomic organization of the defensins HNP-1, 2, 3, 4 and HD-5 and 6 led Bevins et al. (1995) to an evolutionary model attempting to relate the chromosomal organization of the family, and the homologous fractions of each pair of genes.

It is finally advantageous to note that the chromosomal region 8p23 is involved in numerous pathologies, in particular cancer pathologies: there may be mentioned, for example, hepatocellular carcinoma (Becker et al., 1996), non-small cell lung cancer (Sundareshan and Augustus, 1996), prostate cancer (Ichikawa et al., 1996), and colorectal carcinome (Yaremko et al., 1994). Although this has never been documented, it is possible that a deficiency in either of the human defensins has a role in the predisposition to such pathologies, or in their development.

The present invention relates to a novel human defensin, Def-X, which is homologous to defensin HNP-4.

The subject of the present invention is therefore an isolated polypeptide chosen from the following polypeptides:

a) polypeptide whose amino acid sequence is the sequence SEQ ID No. 3;

b) homologous, variant or modified polypeptide of the polypeptide whose amino acid sequence is the sequence SEQ ID No. 3;

c) polypeptide whose amino acid sequence is the amino acid sequence of a biologically active fragment of a polypeptide as defined in a) or b);

d) polypeptide comprising at least one fragment as defined in c).

In the present description, <<polypeptide>> will also be intended to designate a proteine or a peptide.

According to a preferred embodiment, the polypeptide according to the invention is characterized in that it consists of at least one of the following fragments:

a) signal peptide whose aminoacid sequence is the sequence SEQ ID No. 4, corresponding to the sequence between position 1 and position 19, ends included, of the aminoacid sequence SEQ ID No. 3;

b) proregion whose aminoacid sequence is the sequence SEQ ID No. 5, corresponding to the sequence between position 20 and position 63, ends included, of the aminoacid sequence SEQ ID No. 3;

c) mature peptide whose aminoacid sequence is the sequence SEQ ID No. 6, corresponding to the sequence between position 64 and position 94, ends included, of the aminoacid sequence SEQ ID No. 3; or d) homologous, variant or modified fragment of a peptide according to a), b) or c).

Still preferably, the polypeptides according to the present invention correspond to the primary structure of the mature defensin defined above, that is to say the structure corresponding to the following aminoacid sequence SEQ ID No. 6:

Ile Cys His Cys Arg Val Leu Tyr Cys Ile Phe Gly Glu His Leu Gly Gly Thr Cys Phe Ile Leu Gly Glu Arg Tyr Pro Ile Cys Cys Tyr its homologs, variants or modified forms as well as their biologically active fragments and the polypeptides containing them.

It is clearly understood that the polypeptides of the invention are in a nonnatural form, that is to say that they are not taken in their natural environment but that they may have been obtained by purification from natural sources or obtained by genetic recombination or by chemical synthesis as will be described below.

<<Homologous polypeptide>> is understood to mean a polypeptide whose aminoacid sequence exhibits at least 80%, and preferably 90%, of aminoacids in common.

<<Variant polypeptide>> is intended to designate a mutated polypeptide or a polypeptide corresponding to a polymorphism which may exist, in particular in human beings and which may exhibit a truncation, a substitution, a deletion and/or an addition of at least one aminoacid compared with the polypeptide according to the invention.

<<Modified polypeptide>> is understood to designate a polypeptide obtained by genetic recombination or by chemical synthesis as will be described below, exhibiting a modification relative to the normal sequence. These modifications may in particular apply to the pre, pro- or mature domains of the polypeptide according to the invention, the aminoacids responsible for a specificity of spectrum or of efficacy of activity, or responsible for the structural conformation, the charge or the hydrophobicity, and the multimerization and membrane insertion of the polypeptide according to the invention. It is thus possible to create polypeptides with equivalent, increased or reduced activity, and with equivalent, lower or broader specificity. The modifications may also apply to the sequences involved in the maturation, transport and addressing of the polypeptide.

<<Biologically active fragment>> of a polypeptide according to the invention is intended to designate a polypeptide fragment which has conserved at least one activity of the polypeptide from which it is derived, in particular:

capable of being recognized by an antibody specific for a polypeptide according to the invention; and/or capable of acting as an antibiotic; and/or capable of acting as an cytotoxic agent; and/or capable of acting as an antitumor agent; and/or capable of modulating tissue repair, endocrine regulation or the inflammatory process, in particular during an infection.

According to the invention, the biologically active fragments of the polypeptides according to the invention will have a minimum of 10 amino acids, preferably 15 amino acids.

As has been indicated above, among the biologically active fragments, a preferred fragment is the mature peptide having the aminoacid sequence SEQ ID No. 6.

Among the homologs of the mature peptide, there should be mentioned the polypeptides in which up to 5 amino acids have been modified, truncated at the N- or C-terminal end, or deleted, or added, which represents about 80% of the sequence.

The biologically active fragments of this mature peptide preferably comprise from 10 to 15 aminoacids, the advantage of which may be being able to be easily obtained by chemical synthesis.

As indicated, the objective of the modifications of the mature polypeptide will be in particular:

to modulate the activity of the defensin, to modify its specificity, both at the level of the microorganisms on which it is active and on its tissue localization, to modify its bioavailability.

The preceding compounds may be obtained using combinatorial chemistry, in which it is possible to systematically vary portions of the polypeptide before testing them on models, cell cultures or microorganisms, for example, in order to select the compounds which are most active or which have the desired properties.

Chemical synthesis also has the advantage of being able to use:

nonnatural aminoacids, or nonpeptide bonds.

Thus, to enhance the lifespan of the peptides, it may be advantageous to use nonnatural aminoacids, for example in D form, or aminoacid analogs, in particular sulfur-containing forms for example.

Finally, the structure of the mature defensin or of its homologs, variants or modified forms, as well as the corresponding fragments, may be integrated into chemical structures of the polypeptide type and the like. Thus, it may be advantageous to provide at the N- and C-terminal ends compounds not recognized by proteases.

The invention also comprises the nucleic acids encoding a polypeptide according to the invention.

According to a preferred embodiment, the nucleic acids according to the invention will be chosen from the following nucleic acids:

a) nucleic acid having the sequence SEQ ID No. 1 (genomic);

b) nucleic acid having the sequence SEQ ID No. 2 (cDNA);

c) equivalent, homologous, mutated or modified nucleic acid, compared with the nucleic acids according to a) or b);

d) fragments of the sequences a), b) or c) having at least ten bases;

e) nucleic acid capable of hybridizing with one of the sequences as defined in a), b), c) or d).

It is understood that the present invention does not relate to the genomic sequences in their natural chromosomal environment; they are sequences which have been isolated, that is to say that they have been recovered directly or indirectly, their environment having been at least partially modified.

They may thus be genomic DNA, cDNA or RNA comprising nonnatural nucleotides or not; they may also be isolated natural nucleic acids, or synthetic nucleic acids.

Equivalent nucleic acid will be understood to mean a nucleic acid encoding the polypeptides according to the invention, taking into account the degeneracy of the genetic code, and the corresponding cDNAs and RNAs.

Homologous nucleic acids will be understood to mean nucleic acid whose sequence exhibits at least 80%, preferably 90%, homology with the nucleic sequences according to the invention.

Mutated nucleic acid will be understood to mean any nucleic acid encoding a variant polypeptide according to the invention, and any nucleic acid comprising, compared with the sequences SEQ ID No. 1 and SEQ ID No. 2, at least one mutation in the promoter and/or regulatory sequences which may have an effect on the expression of the polypeptide, in particular on its level of expression and the tissue-specificity thereof. The sequences exhibiting a polymorphism which is present in human beings are therefore included in the invention. Among these polymorphisms, some may lead to immune deficiencies, in the response to infections, to predispositions to and/or to the development of cancers.

Modified nucleic acid will be understood to mean any nucleic acid encoding a modified polypeptide according to the invention, or any nucleic acid obtained by mutagenesis according to techniques well known to persons skilled in the art, and comprising modifications relative to the normal sequences, in particular mutations in the regulatory and/or promoter sequences, in particular leading to a modification in the level and/or the tissue-specificity of the expression of the polypeptide.

The present invention relates to all the primers and probes, which may be labeled according to methods well known to persons skilled in the art, which make it possible to identify, in particular by techniques based on hybridization or on amplification, for example by PCR, the nucleic sequences according to the invention, including discriminating between the normal sequences and the mutated sequences.

Among the nucleic acid fragments of interest, there should be mentioned in particular the antisense oligonucleotides, that is to say whose structure ensures, by hybridization with the target sequence, inhibition of the expression of the corresponding product. The sense oligonucleotides should also be mentioned which, by interacting with proteins involved in the regulation of the expression of the corresponding product, will induce either an inhibition, or an activation of this expression.

They may be sequences which act both at the level of the exon or intron sequences described and on the flanking sequences, in particular the promoters and/or 5' UTR regions.

The present invention also relates to cloning or expression vectors comprising a nucleotide sequence as described above.

These cloning or expression vectors may comprise elements ensuring expression of the sequence in a host cell, in particular promoter sequences and regulatory sequences which are effective in said cell.

It being possible for the vector in question to be autonomously replicating or to be intended to ensure the integration of the sequence within the chromosomes of the host cell.

In the case of autonomously-replicating systems, depending on the host cell, either prokaryotic or eukaryotic, systems of the plasmid type or viral systems will be preferably used, it being possible for the vector viruses to be in particular advenoviruses (Perricaudet et al., 1992), retroviruses, poxviruses or herpesviruses (Epstein et al., 1992). Persons skilled in the art know the technologies which can be used for each of these viruses.

Thus, it is known to use, as viral vector, defective viruses whose culture is carried out in complementation cells, this avoiding the possible risks of prolifeation of an infectious viral vector.

When the integration of the sequence into the chromosomes of the host cell will be desired, it will be necessary to provide, on either side of the nucleotide sequence to be integrated, one or more sequences derived from the host cell in order to ensure the recombination. These are also methods which are widely described in the prior art. It will be possible, for example, to use systems of the plasmid or viral type;

such viruses will be, for example, retroviruses (Temin, 1986) or the AAVs, Adenovirus-Associated Virus (Carter, 1993).

The invention also relates to the prokaryotic or eukaryotic cells transformed with a vector as described above in order to ensure the expression of a natural, normal or variant, or modified defensin Def-X, or for example, of one of its fragments.

As indicated above, the present invention also relates to the polypeptides obtained by culturing the cells thus transformed and recovering the protein expressed, it being possible for said recovery to be carried out intracellularly or extracellularly in the culture medium when the vector has been designed to ensure the secretion of the protein by means, for example, of a "signal" sequence, the polypeptide being in the form of a pre-polypeptide or prepropolypeptide. The constructs allowing the secretion of the polypeptides are known, both for prokaryotic systems and for eukaryotic systems. In the context of the present invention, some of the polypeptides Def-X may comprise their own secretory or membrane insertion system.

It is clearly understood that the recombinant polypeptides according to the invention may be obtained in glycosylated or nonglycosylated form and may have the natural tertiary structure or not.

Among the cells which can be used for the production of these polypeptides, there should of course be mentioned bacterial cells (Olins and Lee, 1993), but also yeast cells (Buckholz, 1993), as well as animal cells, in particular mammalian cell cultures (Edwards and Aruffo, 1993) but also insect cells in which methods using baculoviruses, for example (Luckow, 1993), may be used.

The cells thus obtained can make it possible to prepare natural, variant or modified polypeptides, Def-X, but also fragments of these polypeptides, in particular polypeptides which may correspond to the biologically active fragments.

The present invention relates, in addition, to the same polypeptides according to the invention but which are obtained by chemical synthesis and which may comprise nonnatural or modified aminoacids.

The polypeptides according to the present invention, in particular mature defensin, as well as the homologs, derivatives or modified mature polypeptides, may be obtained by chemical synthesis using any one of the numerous peptide syntheses known, for example the techniques using solid phases or techniques using partial solid phases, by condensation of fragments or by a conventional synthesis in solution.

When the compounds according to the present invention are synthesized by the solid phase method, the C-terminal aminoacid is attached to an inert solid support and comprises groups protecting its amino group at the alpha position (and if necessary, protections on its functional side groups).

At the end of this step, the group for protecting the amino terminal group is removed and the second aminoacid, which also comprises the necessary protection, is attached.

The N-terminal protecting groups are removed after each aminoacid has been attached; on the other hand, the protection is of course maintained on the side chains.

When the polypeptide chain is complete, the peptide is cleaved from its support and the protective side groups are removed.

The solid phase synthesis technique is described in particular in Stewart et al. (1984) and Bodanszky (1984).

The details of the synthesis will not be mentioned here; it should simply be recalled that the protective groups which are preferred for the alpha-amino groups are protective groups of the urethane type (BOC or FMOC). As regards the coupling reagents, they are very numerous; among them, there should of course be mentioned more particularly N,N'-diisopropylcarbodiimine (DIC) which is used in general in DMF or DCM.

When it will be desirable to use nonnatural aminoacids, it may be necessary to provide other types of reagent and in particular other types of protection system.

The present invention also relates to polyclonal or monoclonal antibodies obtained by immunological reaction in a human or animal body with an immunogenic agent consisting of a polypeptide according to the invention, in particular a polypeptide obtained by culturing one of the cells which have just been described, or by chemical synthesis as indicated above.

The invention therefore extends to the monoclonal and polyclonal antibodies or one of their fragments, chimeric antibodies, which are capable of specifically recognizing a polypeptide according to the invention.

The invention also comprises the antibodies according to the invention, characterized in that they labeled.

The labeled antibodies may be, for example, immunoconjugated with enzymes such as peroxidase or alkaline phosphatase, or labeled with the aid of fluorescent compounds, biotin or radiolabeled. The labeling techniques are well known to persons skilled in the art and will not be developed in the present description.

The invention also extends to the use of a polypeptide according to the invention as antimicrobial, in particular antibacterial, antifungal, antiviral and/or antiparasitic agent, as cytotoxic agent, in particular for anticancer use, and/or as agent for modulating inflammatory, tissue repair and endocrine, in particular corticostatic, regulating processes.

According to another aspect, the invention relates to a pharmaceutical composition comprising a polypeptide according to the invention, which may be combined with a pharmaceutically acceptable vehicle.

Such a composition may be administered by the systemic, local or topical route.

Its mode of administration, its dosage, its optimal galenic forms may be determined according to the criteria generally taken into account in establishing a treatment appropriate for a patient, in particular their age, their body weight, tolerance of treatment, its observed side effects, and the like.

The invention also comprises a pharmaceutical composition comprising a vector according to the invention which is capable of expressing in vivo a polypeptide according to the invention, which may be combined with a pharmaceutically acceptable vehicle.

It is also possible to envisage the expression of polypeptides or their fragments in vivo, in particular by means of gene therapy and using the vectors which were described above.

In the context of gene therapy, it is also possible to envisage the use of the sequences of the genes or of the cDNAs described above, <<naked>>, this technique was in particular developed by the company Vical, which has shown that it was, under these conditions, possible to express the polypeptide in some tissues without having recourse to the support of a viral vector in particular.

Still in the context of gene therapy, it is also possible to envisage the use of cells transformed ex vivo, which cells may then be reimplanted, either as such, or inside systems of the organoid type, as is also known in the state of the art (Danos et al., 1993). It is also possible to envisage the use of agents facilitating the targeting of a defined cell type, penetration into the cells or transport to the nucleus.

Said pharmaceutical compositions are, according to the invention, intended for the prevention and/or treatment of microbial infections, in particular microbial infections of bacterial, Gram-positive or Gram-negative bacteria, mycobacterial, fungal and viral origin, or parasitic, in particular spirochet, infections.

According to a preferred embodiment, the invention advantageously relates to the pharmaceutical compositions according to the invention, characterized in that the viral infections are infections linked to enveloped viruses, in particular the HSV and HIV viruses.

The subject of the invention is also pharmaceutical compositions according to the invention, intended for the prevention and/or treatment of cancers, in particular melanomas, liver, prostate or non-small cell lung cancer or colorectal carcinoma.

The invention comprises, in addition, pharmaceutical compositions according to the invention, intended to increase the immune defenses, to increase the immune defenses in the case of acquired immunodeficiency or to prevent the immunodeficiency, in particular for the treatment of psoriasis, or to modulate the inflammatory processes in cases in particular of chronic inflammatory diseases.

The polypeptides according to the present invention can be more particularly used in external topical form, for example on the skin and the mucous membranes. These external topical forms may be for pharmaceutical, dermatological or cosmetic use.

In particular, these compositions may be used as pharmaceutical antiseptic agent or as antiseptic in some cosmetics, either for cleansing the skin or superficial body growths and/or as preservative for the compositions.

The topical compositions according to the present invention may be used in particular in some skin, eye, vaginal or buccal conditions. They may also be used as additional cosmetic agent, in particular in some treatment shampoos.

The invention also relates to the detection of the absence or of an abnormal quantity of protein or of nucleic acid corresponding to defensin X as marker of an infection or of pathologies which will be described below.

The invention also relates to the detection of an abnormal form of the protein or the presence of an abnormal nucleic acid corresponding to a mutated defensin which may possibly be completely inactive. In this case, the presence of this abnormal form may be a marker of predisposition to certain conditions, in particular immunodeficiency and/or cancers.

Accordingly, the present invention relates to a method of diagnosing of an immunodeficiency and/or of a predisposition to certain types of cancer, characterized in that the presence of an abnormal defensin and/or of a sequence encoding an abnormal defensin is detected in a sample from a patient.

The diagnostic methods according to the present invention allow in particular the detection of an immunodeficiency and/or of a predisposition to one or more cancers, in particular those cited above, in particular in at-risk families. This type of diagnosis will in general be carried out by the detection of the mutated forms of the protein or of the nucleic acid sequences.

However, the invention also relates to methods for the diagnosis of inflammation, immunodeficiency, predisposition to conditions of the cancer type and/or infections due to microorganisms or linked to an immune deficiency or inflammatory phenomenon, characterized in that they comprise assaying a polypeptide or a nucleic acid according to the invention in a biological sample and comparing the result of said assay which is obtained with the quantity of polypeptide or nucleic acid normally present in an equivalent biological sample.

In this case, the peptide assay will allow, in general, detection of a microbial or parasitic infection and/or of an inflammation. The peptide assays may be carried out by any known method, ELISA or RIA for example. The detection of an abnormal form of defensin-X may be carried out, for example, with the aid of a monoclonal antibody which is specific for this form, in particular the antibodies which are the subject of the invention.

According to a preferred embodiment, the invention advantageously comprises the methods characterized in that they use an oligonucleotide probe and/or primer according to the invention.

The methods in which all or part of the sequence corresponding to the polypeptide Def-X is amplified beforehand by assaying nucleic acid according to the invention will be generally preferred, it being possible for these amplification methods to be carried out by the so-called PCR or PCR-like methods. PCR-like will be understood to designate all the methods using direct or indirect reproductions of the nucleic acid sequences, or in which the labeling systems have been amplified, these techniques are of course known; in general, they involve the amplification of DNA by a polymerase; when the original sample is an RNA, it is advisable to carry out a reverse transcription beforehand. There are currently very numerous methods which allow this amplification, for example the so-called NASBA "Nucleic Acid Sequence Based Amplification" (Compton, 1991), TAS "Transcription based Amplification System" (Guatelli et al., 1990), LCR "Ligase Chain Reaction" (Landegren et al., 1988), "Endo Run Amplification" (ERA), "Cycling Probe Reaction" (CPR), and SDA "Strand Displacement Amplification" (Walker et al., 1992), methods which are well known to persons skilled in the art.

The invention relates, in addition, to diagnostic kits or boxes for the determination of a microbial or parasitic infection, an inflammation, an immunodeficiency and/or a predisposition to cancer-type conditions, characterized in that they comprise an antibody according to the invention.

The diagnostic kits or boxes for the determination of a microbial or parasitic infection, an inflammation, an immunodeficiency and/or predisposition to cancer-type conditions, characterized in that they comprise a probe and/or a primer according to the invention are also included in the invention.

Finally, the subject of the invention is the use of a polypeptide according to the invention as pesticide, in particular for the cultivation of plants of industrial interest such as, for example, food plants such as corn, wheat, soybean, rice or rape, fodder plants, fruit trees, grape vine or ornamental plants.

Other characteristics and advantages of the present invention will emerge on reading the examples below, illustrated by the figures whose legends are described below.

Legend to the Figures

FIG. 1

Genomic sequence of hDef-X.

Presented is the entire genomic DNA sequence of hDef-X which exhibits significant homology with the gene encoding hDef-4 (HNP-4).

The sequence has the following sites, the presence of which is deduced by homology with the hDef-4 sequence:

| | |
|---|---|
| CAAT box | 1711–1714 |
| TATA box | 1758–1767 |
| mRNA start | 1836 |
| exon 1 | 1836–1874 |
| splicing site 1 | GTCAGT |
| Alu insertion | 2155–2335 |
| L1 fragment insertion | 2710–2780 |
| splicing site 2 | CAG |
| exon 2 | 3394–3577 |
| start of coding phase | 3406 |
| splicing site 3 | GTGAGA |
| splicing site 4 | CAG |
| exon 3 | 4164–4379 |
| end of coding phase | 4276 |
| polyadenylation site | 4374–4379. |

FIG. 2

Alignment of the genomic sequences of the human defensins Def-X and Def-4 (HNP-4).

Alignment of the entire genomic DNA sequence of the novel defensin Def-X exhibiting homology with the genomic DNA of hDef-4 (GenBank accession number U18745).

The annotations present the positions on the hDef-4 sequence of the signals CAAT box, TATA box, splicing sites, beginning and ends of introns/exons, start of transcription and polyadenylation site.

FIG. 3

Alignment of the cDNA sequences of hDef-4 (HNP-4) and hDef-X.

The sequences exhibit an overall homology of 61.4%. The alignment reveals an insert of about 75 bases downstream of a STOP codon, which are present on the sequence of hDef-4, but not on that of hDef-X; the strong homology continues on the whole region between the end of this insert and that of the cDNA. Outside this insertion region, the degree of homology between nucleic sequences is therefore remarkable.

FIG. 4

Peptide sequence of the protein hDef-X.

The position of the sites of cleavage of the signal peptide and of the pro region were deduced from the alignment of the peptide sequences of hDef-4 and hDef-X.

FIG. 5

Alignment of the peptide sequences of the known human defensins hDef-1, hDef-4, hDef-5, and hDef-6 with hDef-X.

* The star indicates an amino acid which is conserved on the five sequences.
* The dot indicates an amino acid whose class is conserved on the five sequences (amino acid which is either identical, or which is the subject of a conservative substitution).
^ six arrows indicate the positions of the six cysteines conserved across the class of conventional defensins and responsible for the three-dimensional structure necessary for the activity of these peptides.

EXAMPLES

Example 1

Identification of the Gene Encoding hDef-X

Isolation of BAC B0725 B12

To analyze the 8p23 region of the human genome, in particular in the region known to carry genes encoding human defensins, a BAC ("Bacterial Artificial Chromosome") corresponding to said region was isolated. A BAC library covering the complete human genome was prepared from the ADN of a human lymphoblastic line derived from individual No. 8445 of the CEPH families. This line was used as source of high-molecular weight DNA. The DNA was partially digested with the restriction enzyme BamHI, and then cloned at the BamHI site of the plasmid pBeloBacII. The clones thus obtained were "pooled" and screened according to the three-dimensional analytical procedure previously described for the screening of YAC ("Yeast Artificial Chromosome") libraries (Chumakov et al., 1992 and 1995). The three-dimensional pools obtained were screened by PCR with the aid of the primers flanking the marker SHGC-10793, for Neutrophil defensin 4 precursor (GeneBank: accession number U18745); a clone of BAC B0725 B12 was thus isolated.

After digestion with the restriction enzyme NotI, the size of the insert carried by this BAC was determined on a 0.8% agarose gel after migration by alternating field electrophoreses (CHEF) (4 hours at 9 volts/cm, with an angle of 100°, at 11° C. in 0.5×TAE buffer). It was thus demonstrated that BAC B07025B12 carries an insert of 220 kb, with an internal site for the enzyme NotI.

Chromosomal Location of BAC B0725B12 by Fluorescent in situ Hybridization (FISH)

The chromosomal location of BAC in the candidate region 8p23.1–23.2 was confirmed by fluorescent in situ hybridization (FISH) on metaphase chromosomes, according to the method described by Cherif et al., (1990).

Sequencing of the BAC B0725B12 Insert

To sequence the BAC B0725B12 insert, a subclone library was prepared from the sonicated DNA of this BAC.

The cells derived from one liter of "overnight" culture were treated by alkaline lysis according to conventional techniques. After centrifugation of the product obtained in a cesium chloride gradient, 12 μg of BAC B0725B 12 DNA were purified. 3 μg of DNA were sonicated in order to obtain fragments whose sizes are uniformly distributed from 1.2 kb to 1.5 kb. The fragments obtained were treated in a volume of 50 μl with 2 units of Vent polymerase for 20 minutes at 70° C., in the presence of the 4 deoxytriphosphates (100 μM). The fragments with blocked ends resulting from this step were separated by electrophoreses on a 1% low-melting point agarose gel (60 volts for 3 hours). The fragments grouped according to their sizes were excised and the bands obtained treated with agarose. After extraction with chloroform and dialysis on Microcon 100 columns, the DNA in solution was adjusted to a concentration of 100 ng/μl. A ligation was performed "overnight" by bringing 100 ng of fragmented DNA of BAC B0725B12 into contact with 20 ng of DNA of the vector BluescriptSK linearized by enzymatic digestion, and treated with alkaline phosphatase. This reaction was carried out in a final volume of 10 μl in the presence of 40 units/μl of T4 DNA ligase (New England Biolabs). The ligation products then served to transform, by electroporation either a strain XL-Blue (for the multicopy plasmids), or a D10HB strain (for the subclones derived from BAC). The lacZ⁻ clones which are resistant to the antibiotic were subcultured individually in microplates for storage and sequencing.

960 subclones corresponding to the insertion of fragments of 1.2 kb to 1.5 kb at the BamHI site (made blunt) of the plasmid BluescriptSK.

The inserts of these subclones were amplified by PCR on bacterial cultures performed "overnight", using the vector primers flanking the inserts. The sequence of the ends of these inserts (average 500 bases on each side) was determined by automated fluorescent sequencing on an ABI 377 sequencer equipped with the ABI Prism DNA Sequencing Analysis software (version 2.1.2).

The fragments having a sequence obtained from the sub-BACs were assembled by the Gap4 software of R. Staden (Bonfield et al., 1995). This software allows the reconstruction of a complete sequence from fragments of sequences. The sequence deduced from the alignment of the different fragments is the consensus sequence.

Finally, directed sequencing techniques (systematic primer walking) were used to perfect the sequences and to link the contigs.

Analysis of the Sequences for the Identification of Genes

The potential exons of the insert of BAC B0725B12 were located by searching for homology on public protein, nucleic acid and EST (Expressed Sequence Tag) banks.

Databanks

Local refusions of the principal public banks were used. The protein bank used consists of the nonredundant fusion of the libraries Genpept (automatic translation of GenBank, NCBI; Benson et al., 1996); Swissprot (George et al., 1996) and PIR/NBRF (Bairoch et al., 1996). The doublets were eliminated by the "nrdb" software (public domain, NCBI; Benson et al., 1996). The internal repeats were then masked by the "xnu" software (public domain, NCBI; Benson et al., 1996). The resulting bank, called NRPU (Non-Redundant Protein-Unique) served as reference for the searches for protein homologies. The homologies found with this bank made it possible to locate regions potentially encoding a protein fragment which is at least related to a known protein (coding exons). The EST bank used is composed of the subsections "gbest" (1–9) of Genbank (NCBI; Benson et al., 1996). It contains all the fragments of public transcripts.

The homologies found with this bank made it possible to locate potentially transcribed regions (present on the messenger RNA).

The nucleic acid bank (other than the ESTs) used contains all other subsections of Genbank and of EMBL (Rodriguez-Tome et al., 1996) whose doublets were eliminated as above.

Softwares

All the BLAST softwares (Altschul et al., 1990) for searching for homologies between a sequence and protein or nucleic databanks were used. The significance levels used depend on the length and on the complexity of the region tested as well as on the size of the reference bank. They were adjusted and adapted to each analysis.

Example 2

Analysis of the Nucleic and Peptide Sequences of hDef-X

Structure of the Gene Encoding hDef-X

The alignment of the gene encoding hDef-X with those encoding the known defensins made it possible to note a maximum homology between hDef-X and hDef-4 (FIG. 2). The overall level of homology between the two nucleic sequences is 72%. The only two regions of the genomic DNA of hDef-X which do not exhibit homology with that of hDef-4 correspond to two regions of insertion of a sequence which is repeated in the sequence of hDef-X, which are absent from the sequence of hDef-4: one element of the Alu type (positions 2155 to 2335) and one fragment of element of Line 1 (positions 2710 to 2780).

A high conservation of the region flanking in 5' the promoter region is noted, from which a high conservation of the elements for regulating the stability of the messenger and the expression of the gene probably results.

The high conservation of the sequence of exon 1, which is not translated, makes it possible to definitively attach the defensin hDef-X to the class of hematopoietic conventional defensins, that is hDef-1, 2, 3 and 4, in contrast to the enteric defensins hDef-5 and 6, whose genomic sequence comprises only two exons, both of which are coding.

The alignment of the cDNAs for hDef-4 and hDef-X, indicating a homology greater than 60%, is presented in FIG. 3.

Protein Analysis

The peptide sequence of the defensin according to the invention is represented in FIG. 4. The three domains of the protein are positioned as follows:

signal peptide: aa 1–19 pro region: aa 20–63 mature peptide: aa 64–94.

The specific degrees of homologies between hDef-4 and hDef-X were calculated, according to the relevant region of the protein:

signal peptide: 63.2% proregion: 52.3% mature peptide: 37.9%.

The overall homology is 49.5%. These figures confirm the very high homology which exists between defensins, a homology which is maximum at the level of the signal peptides and minimum at the level of the mature peptides.

The amino acids conserved in the class of conventional defensins are found in the primary protein sequence of Def-X, in particular the six cysteines involved in the three-dimensional structure thereof (FIG. 5).

In order to predict the secondary structures present on the defensin according to the invention, softwares for predicting secondary structure which are included in the Protein Interpretation Package, Copyright MRC 1994, Medical Research Council, Hillsroad, Cambridge, United Kingdom, were used.

These softwares made it possible in particular to compare the predicted structures of Def-X and HNP-4. Hydrophobicity profiles, alpha-helix structures, β sheets, amphiphilicity are superposable in the two peptides, which suggests similar processes for membrane insertion and for formation of multimeric ion channels for these two defensins.

Example 3

Search for Mutations Associated with Familial Cancer Cases

Extraction of the Genomic DNA

The genomic DNA of immunodeficient or cancer patients is extracted from the peripheral venous blood after cellular lysis, protein digestion, organic partition and finally alcohol precipitation, according to conventional techniques well known to persons skilled in the art.

It is in particular advantageous to study the presence of mutations in the genomic DNA of individuals coming from families with a high rate of cancer, all types of cancer combined. A deficiency in a gene for granulocyte defensin, such as hDef-X, can in fact have a role in predisposition to cancers, as mentioned above.

Amplification of the Genomic DNA

Oligonucleotide primers are used for the genomic amplification of the exon sequences derived from BAC B0725B12; they are predicted by computer analysis, and defined with the aid of the OSP software (Hillier et al., 1991).

All these primers contain, upstream of the bases specifically targeted by the amplification, a common universal oligonucleotide tail intended to allow the sequencing of the amplified fragments (PU: 5'-TGTAAAACGACGGCCAGT-3' for the upstream primers, and RP: 5'-CAGGAAACAGCTATGACC-3' for the downstream primers).

The oligonucleotide primers are synthesized according to the phosphoramidite method, on a GENSET UFPS 24.1 synthesizer.

The amplification of each predicted exon sequence is carried out by polymerase chain reaction (PCR), under the following conditions:

| | |
|---|---|
| Final volume | 50 μl |
| Genomic DNA | 100 ng |
| MgCl2 | 2 mM |
| dNTP (for each) | 200 μM |
| Primer (for each) | 7.5 pmoles |
| AmpliTaq Gold DNA polymerase (Perkin) | 1 unit |
| PCR buffer (10X = 0.1M Tris HCl pH 8.3, 0.5M KCl) | 1 X. |

The amplification is carried out in a Perkin Elmer 9600 or MJ Research PTC200 thermocycler with a heating cover. After heating at 94° C. for 10 minutes, 35 cycles are performed. Each cycle comprises: 30 seconds at 94° C., 1 minute at 55° C. and 30 seconds at 72° C. A final segment of elongation of 7 minutes at 72° C. ends the amplification.

The quantity of amplification products obtained is determined on a 96-well microplate, by fluorometry, using the Picogreen intercalating agent (Molecular Probes).

Detection of the Polymorphisms/mutations

The products of genomic amplification by PCR are sequenced on the ABI 377 automated sequencer using fluorescent primers labeled with ABI fluorochromes (Joe, Fam, Rox and Tamra) and Thermosequanase DNA polymerase (Amersham).

The reactions are carried out in 96-well microplates, on a Perkin Elmer 9600 thermocycler, under conventional temperature cycle conditions:

8 cycles: denaturation: 5 sec. at 94° C.; annealing: 10 sec.; extension: 30 sec. at 72° C., and then 13 cycles: denaturation: 5 sec. at 94° C.; extension: 30 sec. at 72° C.

6 units of Thermosequanase, and 5–25 ng of amplification product are used per sequence reaction.

At the end of the amplification cycles, the products of the sequence reactions are precipitated from ethanol, resuspended in loading buffer containing formamide, denatured, and deposited on 4% acrylamide gels; the electrophoreses (2 hours 30 min at 3000 volts) are conducted on ABI 377 sequencers equipped with ABI sofiwares for collection and analysis (ABI Prism DNA Sequencing Analysis Software, version 2.1.2.).

The sequences obtained in patients suffering from the deficiencies studied, in particular in patients from families with a high predisposition to cancers, are compared with the sequences obtained in control subjects, related or not related. A statistical analysis (lod score calculation) makes it possible to conclude as to the significance of the presence of a site of heterozygosity and to its association with a predisposition to cancers.

Example 4

Search for point Mutations

The point mutations identified as indicated above can then be detected in patients having a potential deficiency in the gene encoding hDef-X, according to numerous methods known to persons skilled in the art. Among these, the following nonexhaustive lists may be mentioned:

sequencing

<<single nucleotide primer extension>> (Syvanen et al., 1990)

RFLP search for <<single strand conformation polymorphism>> methods based on a cleavage of the mismatched regions (enzymatic cleavage with S1 nuclease, chemical cleavage with various compounds such as piperidine or osmium tetroxide)

detection of heteroduplex in electrophoresis methods based on the use of <<allele specific oligonucleotide>> (ASO, Stoneking et al., 1991)

OLA method (<<dual color oligonucleotide ligation assay, Samiotaki et al., 1994)

ARMS (<<amplification refractory mutation system>>), or ASA (<<allele specific amplification>>), or PASA (<<PCR amplification of specific allele>>) (Wu et al., 1989), method.

REFERENCES

Altschul, Stephen F., Gish W., Miller W., Myers E. W., & Lipman D. J. Basic local alignment search tool. J. Mol. Biol. 215:403–10 (1990).

Bairoch A. & Apweiler R. The SWISS-PROT protein sequence data bank and its new supplement TREMBL. Nucleic Acids Res. 24: 21–25 (1996).

Becker S. A., Zou, Y. Z. & Slagle, B. L. Frequent loss of chromosome 8p in hepatitis B virus-positive hepatocellular carcinomas from China. Cancer Res. 56 (21): 5092–7 (1996).
Benson D. A., Boguski M., Lipman D. J. & Ostell J. GenBank. Nucleic Acids Res. 24:1–5 (1996).
Bodansky M., Principles of peptide synthesis, (1984).
Bevins, C. L., Jones, D. E., Dutra, A., Schaffzin, J. & Muenke, M. Human enteric defensin genes: chromosomal map position and a model for possible evolutionary relationships. Genomics 31: 95–106 (1996).
Bonfield J. K., Smith K. F. & Staden R. A new DNA sequence assembly program. Nucleic Acids Res. 23: 4992–9 (1995).
Buckholz R. G. Yeast Systems for the Expression of Heterologous Gene Products. Curr. Op. Biotechnology 4: 538–542 (1993).
Carter B. J. Adeno-Associated virus vectors. Curr. Op. Biotechnology 3: 533–539 (1993).
Cherif D., Julier C., Delattre O., DerréJ., Lathrop G. M., & Berger R.: Simultaneous localization of cosmids and chromosome R-banding by fluorescence microscopy—Applications to regional mapping of chromosome 11. Proc. Natl. Acad. Sci. USA. 87: 6639–6643 (1990).
Chumakov I., Rigault P., Guillou S., Ougen P., Billault A., Guasconi G., Gervy P., Le Gall I., Soularue P., Grinas P. et al. Continuum of overlapping clones spanning the entire human chromosome 21q. Nature 359: 380–386 (1992).
Chumakov I. M., Rignault P., Le Gall I. et al. A YAC contig map of the human genome. Nature 377 supplt: 175–183 (1995).
Compton J. Nucleic Acid Sequence-Based Amplification. Nature 350: 91–92 (1991).
Danos O., Moullier P. & Heard J. M. Réimplantation de cellules génétiquement modifiées dans des néo-organes vascularisés [Reimplantation of genetically modified cells into vascularized neo-organs]. Médecine/Sciences 9:62–64 (1993).
Edwards C. P. et Aruffo A. Current applications of COS cell based transient expression systems. Curr. Op. Biotechnology 4: 558–563 (1993).
Epstein A.: Les vecteurs herpétiques pour le transfert de génes [Herpetic vectors for gene transfer]—Médecine/Sciences 8: 902–911 (1992).
Ganz T. & Lehrer R. I. Defensins. Curr. Op. Immunology. 6: 584–9 (1994).
Ganz T. & Lehrer R. I. Defensins. Pharmac. Ther. Vol. 66: 191–205 (1995).
George D. G., Barker W. C., Mewes H. W, Pfeiffer F. & Tsugita A. The PIR-International Protein Sequence Database. Nucleic Acids Res. 24: 17–20 (1996).
Guatelli J. C. et al. Isothermal in vitro amplification of nucleic acids by a multienzyme reaction modeled after retroviral replication. Proc. Natl. Acad. Sci. USA 87: 1874–1878 (1990).
Hillier L. & Green P. OSP: a computer program for choosing PCR and DNA sequencing primers. PCR Methods Appl. 1: 124–8 (1991).
Ichikawa, T., Nihei, N., Kuramochi, H., Kawana, Y., Killary, A. M., Rinker-Schaeffer, C. W., Barrett, J. C., Isaacs, J. T., Kugoh, H., Oshimura, M. & Shimazaki, J. Metastasis suppressor genes for prostate cancer. Prostate Suppl. 6: 31–35 (1996).
Kagan, B. L., Ganz, T. & Lehrer, R. I. Defensins: a family of antimicrobial and cytotoxic peptides. Toxicology 87: 131–149 (1994).
Landegren U., Kaiser R., Sanders J. & Hood L. A ligase-mediated gene detection technique. Science 241: 1077–1080 (1988).
Lehrer & Ganz. Defensins: endogenous antibiotic peptides from human leukocytes. Ciba Found. Sympo. 171: 276–290 (1992).
Luckow V. A. Baculovirus systems for the expression of human gene products. Curr. Op. Biotechnology 4: 564–572 (1993).
Mallow, E. B., Harris, A., Salzman, N., Russel, J. P., DeBerardinis, R. J., Ruchelli, E., & Bevins, C. L. Human enteric defensins. Gene structure and developmental expression. J. Biol. Chem. 271 (8): 4038–4045 (1996).
Martin, E., Ganz, T. & Lehrer, R. I. Defensins and other endogenous peptide antibiotics of vertebrates. J. Leukocyte Biol. 58: 128–136 (1995).
Olins P. O. et Lee S. C. Recent advances in heterologous gene expression in E. coli. Curr. Op. Biotechnology 4: 520–525 (1993).
Perricaudet M., Stratford-Perricaudet L., & Briand P.: La thérapie génique par adénovirus [Gene therapy using adenoviruses]—La Recherche 23: 471–473 (1992).
Rodriguez-Tome P., Stoehr P. J., Cameron G. N., & Flores T. P. The European Bioinformatics Institute (EBI) databases. Nucleic Acids Res. 24: 6–12 (1996).
Samiotaki M., Kwiatkowksi M., Parik J., & Landegren U. Dual-color detection of DNA sequence variants through ligase-mediated analysis. Genomics 20: 238–242 (1994).
Sparkes, R. S., Kronenberg, M., Heinzmann, C., Daher, K. A., Klisak, I., Ganz, T. & Mohandas, T. Assignment of defensin gene(s) to human chromosome 8p23. Genomics 5 (2): 240–4 (1989).
Stewart, J. M. et Yound, J. D. Solid Phase Peptides Synthesis. Pierce Chem. Company, Rockford, 111, 2éme éd., (1984).
Stoneking M., Hedgecock D., Higuchi R. G., Vigilant L., & Erlich H. A. Population variation of human DNA control region sequences by enzymatic amplification and sequence-specific oligonucleotide probes. Am. J. Hum. Genet. 48: 370–382 (1991).
Sundareshan, T. S. & Augustus, M. Cytogenetics of non-small cell lung cancer: simple technique for obtaining high quality chromosomes by fine needle aspirate cultures. Cancer Genet. Cytogenet. 91 (1): 53–60 (1996).
Syvänen A.C., Aalto-Setala K., Harju L., Kontula K. & Soderlund H. A primer-guided nucleotide incorporation assay in the genotyping of Apo E. Genomics 8: 684–692 (1990).
Temin H. M.: Retrovirus vectors for gene transfer. In Kucherlapati R., ed. Gene Transfer, New York, Plenum Press, 149–187 (1986).
Walker G. T., Fraiser M. S., Schram J. L., Little M. C., Nadeau J. G., & Malinowski D. P. Strand displacement amplification: an isothermal in vitro DNA amplification technique. Nucleic Acids Res. 20: 1691–1696 (1992).
White, S. H., Wimley, W. C. & Selsted, M. E. Structure, function, and membrane integration of defensins. Curr. Op. Structural Biology. 5: 521–527 (1995).
Wu D. Y., Ugozzoli L., Pal B. K. & Wallace R. B. Allele-specific amplification of b-globin genomic DNA for diagnosis of sickle cell anemia. Proc. Natl. Acad. Sci. USA 86: 2757–2760 (1989).
Yaremko, M. L., Wasylyshyn, M. L., Paulus, K. L., Michelassi, F. & Westbrook, C. A. Deletion mapping reveals two regions of chromosome 8 allele loss in colorectal carcinomas. Genes Chromosomes Cancer. 10 (1): 1–6 (1994).

What is claimed is:

1. An isolated polypeptide selected from the group consisting of:
   a) a polypeptide comprising the sequence of SEQ ID No. 3;
   b) a polypeptide comprising an amino acid sequence at least 80% identical over the full length to the amino acid sequence of SEQ ID No. 3; and
   c) a polypeptide comprising a fragment of at least 10 consecutive amino acids of SEQ ID No. 3;
   wherein said isolated polypeptide has at least one biological activity selected from the group consisting of recognition by an antiody specific for the polypeptide of SEQ ID NO: 3, antimicrobial activity, and cytotoxic activity.

2. An isolated polypeptide comprising:
   a) a signal peptide comprising the sequence of SEQ ID No. 4;
   b) a proregion comprising the sequence of SEQ ID No. 5;
   c) a mature peptide comprising the sequence SEQ ID No. 6;
   d) a polypeptide comprising an amino acid sequence at least 90% identical over the full length to the amino acid sequence of SEQ ID No. 4, SEQ ID No. 5, or SEQ ID No. 6; or
   e) a fragment comprising at least 10 consecutive amino acids of SEQ ID NO: 4, SEQ ID NO. 5, or SEQ ID NO. 6;
   wherein said signal peptide causes intra- or extracellular secretion of a polypeptide and/or is recognized by an antibody specific for the polypeptide of SEQ ID No. 3 or SEQ ID NO: 4;
   wherein said proregion inactivates the precursor form of the defensin molecule and/or provides a support for the acquisition of the active conformation of the mature peptide and/or is recognized by an antibody specific for the polypeptide of SEQ ID No. 3 or SEQ ID NO: 5;
   wherein said mature peptide has at least one biological activity selected from the group consisting of recognition by an antibody specific for the polypeptide of SEQ ID No. 3 or SEQ ID NO: 6, antimicrobial activity, and cytotoxic activity;
   wherein said fragment of SEQ ID No. 4 causes intra- or extracellular secretion of a polypeptide and/or is recognized by an antibody specific for the polypeptide of SEQ ID No. 3 or SEQ ID NO: 4;
   wherein said fragment of SEQ ID No. 5 inactivates the precursor form of the defensin molecule and/or provides a support for the acquisition of the active conformation of the mature peptide and/or is recognized by an antibody specific for the polypeptide of SEQ ID No. 3 or SEQ ID NO: 5; and
   wherein said fragment of SEQ ID No. 6 has at least one biological activity selected from the group consisting of recognition by an antibody specific for the polypeptide of SEQ ID No. 3 or SEQ ID NO 6, antimicrobial activity, and cytotoxic activity.

3. An isolated polypeptide selected from the group consisting of:

a) a polypeptide comprising the sequence of SEQ ID No. 6;
b) a polypeptide comprising an amino acid sequence at least 80% identical over the full length to the amino acid sequence of SEQ ID No. 6; and
c) a polypeptide comprising a fragment of at least 10 consecutive amino acids of the sequence of SEQ ID No. 6
wherein said isolated polypeptide has at least one biological activity selected from the group consisting of recognition by an antibody specific for the polypeptide of SEQ ID NO: 3 or SEQ ID NO: 6, antimicrobial activity, and cytotoxic activity.

4. The isolated polypeptide according to claim 1, wherein said fragment comprises at least 15 consecutive amino acids.

5. A composition comprising a pharmaceutically acceptable vehicle and an isolated polypeptide according to one of claims 1, 2, 3, or 4 in a form suitable for topical administration.

6. The isolated polypeptide according to claim 1 comprising the sequence of SEQ ID No. 3.

7. The isolated polypeptide according to claim 1, wherein said polypeptide comprises an amino acid sequence at least 80% identical over the full length to the amino acid sequence of SEQ ID No. 3.

8. The isolated polypeptide according to claim 1, wherein said isolated polypeptide comprises a fragment of at least 10 consecutive amino acids of the polypeptide of SEQ ID No. 3.

9. The isolated polypeptide according to claim 2, comprising a signal peptide comprising the sequence of SEQ ID No. 4.

10. The isolated polypeptide according to claim 2, comprising a proregion comprising the sequence of SEQ ID No. 5.

11. The isolated polypeptide according to claim 2, comprising a mature peptide comprising the sequence of SEQ ID No. 6.

12. The isolated polypeptide according to claim 2, comprising an amino acid sequence at least 90% identical over the full length to the amino acid sequence of SEQ ID No. 4, SEQ ID No. 5, or SEQ ID No. 6.

13. The isolated polypeptide according to claim 2 comprising a fragment of at least 10 consecutive amino acids of the signal peptide comprising the sequence of SEQ ID No. 4.

14. The isolated polypeptide according to claim 2 comprising a fragment of at least 10 consecutive amino acids of a proregion comprising the sequence of SEQ ID No. 5.

15. The isolated polypeptide according to claim 2 comprising a fragment of at least 10 consecutive amino acids of a mature peptide comprising the sequence of SEQ ID No. 6.

16. The isolated polypeptide according to claim 3, wherein said isolated polypeptide comprises the sequence of SEQ ID No. 6.

17. The isolated polypeptide according to claim 3, wherein said isolated polypeptide comprises an amino acid sequence at least 80% identical over the full length to the amino acid sequence of SEQ ID No. 6.

18. The isolated polypeptide according to claim 3, wherein said isolated polypeptide comprises a fragment of at least 10 consecutive amino acids of the sequence of SEQ ID No. 6.

19. The composition according to claim 5, wherein said isolated polypeptide comprises the sequence of SEQ ID No. 3.

20. The composition according to claim 5, wherein said isolated polypeptide comprises an amino acid sequence at least 80% identical over the full length to the amino acid sequence of SEQ ID No. 3.

21. The composition according to claim 5, wherein said isolated polypeptide comprises a fragment of at least 10 consecutive amino acids of the polypeptide of SEQ ID No. 3.

22. The composition according to claim 5, wherein said isolated polypeptide comprises a signal peptide comprising the sequence of SEQ ID No. 4.

23. The composition according to claim 5, wherein said isolated polypeptide comprises a proregion comprising the sequence of SEQ ID No. 5.

24. The composition according to claim 5, wherein said isolated polypeptide comprises a mature peptide comprising the sequence of SEQ ID 6.

25. The composition according to claim 5, wherein said isolated polypeptide comprises an amino acid sequence at least 90% identical over the full length to the amino acid sequence of SEQ ID No. 4, SEQ ID No. 5, or SEQ ID No. 6.

26. The composition according to claim 5, wherein said isolated polypeptide comprises a fragment of at least 10 consecutive amino acids of the signal peptide comprising the sequence of SEQ ID No. 4.

27. The composition according to claim 5, wherein said isolated polypeptide comprises a fragment of at least 10 consecutive amino acids of a proregion comprising the sequence of SEQ ID No. 5.

28. The composition according to claim 5, wherein said isolated polypeptide comprises a fragment of at least 10 consecutive amino acids of mature peptide comprising the sequence of SEQ ID No. 6.

29. The composition according to claim 5, wherein said isolated polypeptide comprises the sequence of SEQ ID No. 6.

30. The composition according to claim 5, wherein said isolated polypeptide comprises an amino acid sequence at least 80% identical over the full length to the amino acid sequence of SEQ ID No. 6.

31. The composition according to claim 5, wherein said isolated polypeptide comprises a fragment of at least 10 consecutive amino acids of the sequence of SEQ ID No. 6.

32. The isolated polypeptide according to claim 3, wherein said fragment comprises at least 15 consecutive amino acids.

33. The isolated polypeptide according to claim 1, wherein said antimicrobial activity is antifungal, antibacterial, antiviral, and/or antiparasitic.

34. The isolated polypeptide according to claim 2, wherein said antimicrobial activity is antifungal, antibacterial, antiviral, and/or antiparasitic.

35. The isolated polypeptide according to claim 3, wherein said antimicrobial activity is antifungal, antibacteral antiviral, and/or antiparasitic.

36. The isolated polypeptide according to claim 2, wherein said fragment comprises at least 15 consecutive amino acids.

37. The isolated polypeptide according to claim 1, wherein said biological activity is reognition by an antibody specific for the polypeptide of SEQ ID NO: 3.

38. The isolated polypeptide according to claim 1, wherein said biological activity is antimicrobial activity.

39. The isolaed poypeptide according to claim 1, wherein said biological activity is cytotoxic activity.

40. The isolated polypeptide according to claim 3, wherein said biological activity is recognition by an antibody specific for the polypeptide of SEQ ID NO: 3.

41. The isolated polypeptide according to claim 3, wherein said biological activity is antimicrobial activity.

42. The isolated polypeptide according to claim 3, wherein said biological activity is cytotoxic activity.

43. The isolated polypeptide according to claim 2, wherein said signal peptide, or fragment comprising 10 consecutive amino acids thereof, causes intra- or extracellular secretion of a polypeptide.

44. The isolated polypeptide according to claim 2, wherein said signal peptide, or fragment comprising at least consecutive 10 amino acids thereof, is recognized by an antibody specific for the polypeptide of SEQ ID No. 3 or SEQ ID No. 4.

45. The isolated polypeptide according to claim 2, wherein said proregion, or fragment comprising at least 10 consecutive amino acids thereof, inactivates the precursor form of the defensin molecule.

46. The isolated polypeptidc according to claim 2, wherein said proregion, or fragment comprising at least 10 consecutive amino acids thereof, provides a support for the acquisition of the active conformation of the mature peptide.

47. The isolated polypeptide according to claim 2, wherein said proregion, or fragment comprising at least 10 consecutive amino acids thereof, is recognized by an antibody specific for the polypeptide of SEQ ID No. 3 or SEQ ID No. 5.

48. The isolated polypeptide according to claim 2, wherein said mature peptide, or fragment comprising at least 10 consecutive amino acids thereof, has antimicrobial activity.

49. The isolated polypeptide according to claim 2, wherein said mature peptide, or fragment comprising at least 10 consecutive amino acids thereof, has cytotoxic activity.

50. The isolated polypeptide according to claim 2, wherein said mature peptide, or fragment comprising at least 10 consecutive amino acids thereof, is recognized by an antibody specific for the polypeptide of SEQ ID: No. 3 or SEQ ID NO 6.

51. The isolated polypeptide according to claim 12, wherein said isolated polypeptide has an amino acid sequence at least 90% identical over the full length to the amino acid sequence of SEQ ID No. 4.

52. The isolated polypeptide according to claim 12, wherein said isolated polypeptide has an amino acid sequence at least 90% identical over the full length to the amino acid sequence of SEQ ID No. 5.

53. The isolated polypeptide according to claim 12, wherein said isolated polypeptide has an amino acid sequence at least 90% identical over the full length to the amino acid sequence of SEQ ID No. 6.

54. The composition according to claim 25, wherein said isolated polypeptide has an amino acid sequence at least 90% identical over the full length to the amino acid sequence of SEQ ID No. 4.

55. The composition according to claim 25, wherein said isolated polypeptide has an amino acid sequence at least 90% identical over the full length to the amino acid sequence of SEQ ID No. 5.

56. The composition according to claim 25, wherein said isolated polypeptide has an amino acid sequence at least 90% identical over the full length to the amino acid sequence of SEQ ID No. 6.

* * * * *

UNITED STATES PATENT AND TRADEMARK OFFICE
CERTIFICATE OF CORRECTION

PATENT NO. : 6,329,340 B1
DATED : December 11, 2001
INVENTOR(S) : Lydie Bougueleret and Ilya Chumakov It is certified that error appears in the above-identified patent and that said Letters Patent is hereby corrected as shown below:

Column 16,
Line 18, "sofiwares" should read -- softwares --.

Column 30,
Line 15, "SEQ ID 6." should read -- SEQ ID No. 6. --.
Line 59, "reognition" should read -- recognition --.
Line 63, "isolaed poypcptide" should read -- isolated polypeptide --

Column 31,
Line 18, "polypeptidc" should read -- polypeptide --.

Signed and Sealed this

Twenty-fifth Day of June, 2002

Attest:

Attesting Officer

JAMES E. ROGAN
Director of the United States Patent and Trademark Office